(12) United States Patent
Schoenle et al.

(10) Patent No.: US 12,171,458 B2
(45) Date of Patent: *Dec. 24, 2024

(54) SYSTEM, DEVICE, AND METHOD FOR INTERRUPTED DUAL ACTION (SANDING AND CUTTING) FORCES WITH CONTINUAL MACERATION AND ASPIRATION

(71) Applicant: Cardiovascular Systems, Inc., St. Paul, MN (US)

(72) Inventors: Victor L. Schoenle, Greenfield, MN (US); Joseph P. Higgins, Minnetonka, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 159 days.

This patent is subject to a terminal disclaimer.

(21) Appl. No.: 17/870,113

(22) Filed: Jul. 21, 2022

(65) Prior Publication Data

US 2022/0354531 A1     Nov. 10, 2022

Related U.S. Application Data

(62) Division of application No. 16/665,726, filed on Oct. 28, 2019, now Pat. No. 11,406,419.

(Continued)

(51) Int. Cl.
*A61B 17/3207* (2006.01)
*A61B 17/00* (2006.01)
*A61B 17/22* (2006.01)

(52) U.S. Cl.
CPC .......... *A61B 17/320758* (2013.01); *A61B 2017/00778* (2013.01); *A61B 2017/22045* (2013.01); *A61B 2017/22079* (2013.01)

(58) Field of Classification Search
CPC ........ A61B 17/3207; A61B 17/320758; A61B 17/320783; A61B 2017/00778; A61B 2017/22079; A61B 2017/22045
See application file for complete search history.

(56) References Cited

U.S. PATENT DOCUMENTS

| 5,195,956 A | 3/1993 | Stockmeier |
| 6,632,230 B2 | 10/2003 | Barry |

(Continued)

FOREIGN PATENT DOCUMENTS

| CN | 101522116 A | 9/2009 |
| CN | 102056557 A | 5/2011 |

(Continued)

OTHER PUBLICATIONS

International Search Report and Written Opinion issued in related PCT Application No. PCT/US2019/58434, dated Feb. 14, 2020.

(Continued)

*Primary Examiner* — Tuan V Nguyen
(74) *Attorney, Agent, or Firm* — Kagan Binder, PLLC

(57) ABSTRACT

A rotational atherectomy device includes a drive shaft, a cutter mechanism coupled to the drive shaft and configured to cut occlusive material from a lesion, and a multi-stage macerator coupled to the drive shaft and configured to macerate cut occlusive material into a fine slurry. Successive stages of the multi-stage macerator macerate the cut occlusive material into successively smaller particles, which are moved proximally through a lumen of a sheath of the device that surrounds the drive shaft proximal to the macerator. The device may include a movable cutter mechanism guard that is passively rotatable between a first position in which it covers the cutter mechanism and a second position in which it exposes the cutter mechanism. One or more features of the device may limit a depth to which the cutter mechanism is (Continued)

able to cut the occlusive material to reduce a likelihood of undesirable tissue dissection.

37 Claims, 18 Drawing Sheets

Related U.S. Application Data

(60) Provisional application No. 62/752,083, filed on Oct. 29, 2018.

(56) References Cited

U.S. PATENT DOCUMENTS

| | | | |
|---|---|---|---|
| 8,123,703 B2* | 2/2012 | Martin | A61B 17/00234 600/585 |
| 8,361,094 B2 | 1/2013 | To et al. | |
| 9,119,662 B2 | 9/2015 | Moberg | |
| 9,636,138 B2 | 5/2017 | Schneider | |
| 2008/0039883 A1 | 2/2008 | Nohilly | |
| 2009/0270888 A1 | 10/2009 | Patel et al. | |
| 2010/0312263 A1 | 12/2010 | Moberg et al. | |
| 2012/0053606 A1 | 3/2012 | Schmitz et al. | |
| 2012/0109171 A1 | 5/2012 | Zeroni et al. | |
| 2013/0123823 A1 | 5/2013 | Rosenthal | |
| 2014/0222046 A1* | 8/2014 | Schneider | A61B 17/320783 606/159 |
| 2015/0105809 A1 | 4/2015 | Connolly | |
| 2017/0000518 A1 | 1/2017 | Smith et al. | |
| 2018/0110540 A1 | 4/2018 | Palushi et al. | |

FOREIGN PATENT DOCUMENTS

| | | |
|---|---|---|
| CN | 102946815 A | 2/2013 |
| CN | 104768482 A | 7/2015 |
| WO | 2018/119473 A1 | 6/2018 |

OTHER PUBLICATIONS

Notification Concerning Transmittal of Copy of International Preliminary Report on Patentability and International Preliminary Report on Patentability issued in PCT/US2019/058434, dated May 14, 2021.

Extended Search Report issued by the European Patent Office for Application No. 19878081.9, dated Mar. 17, 2022.

* cited by examiner

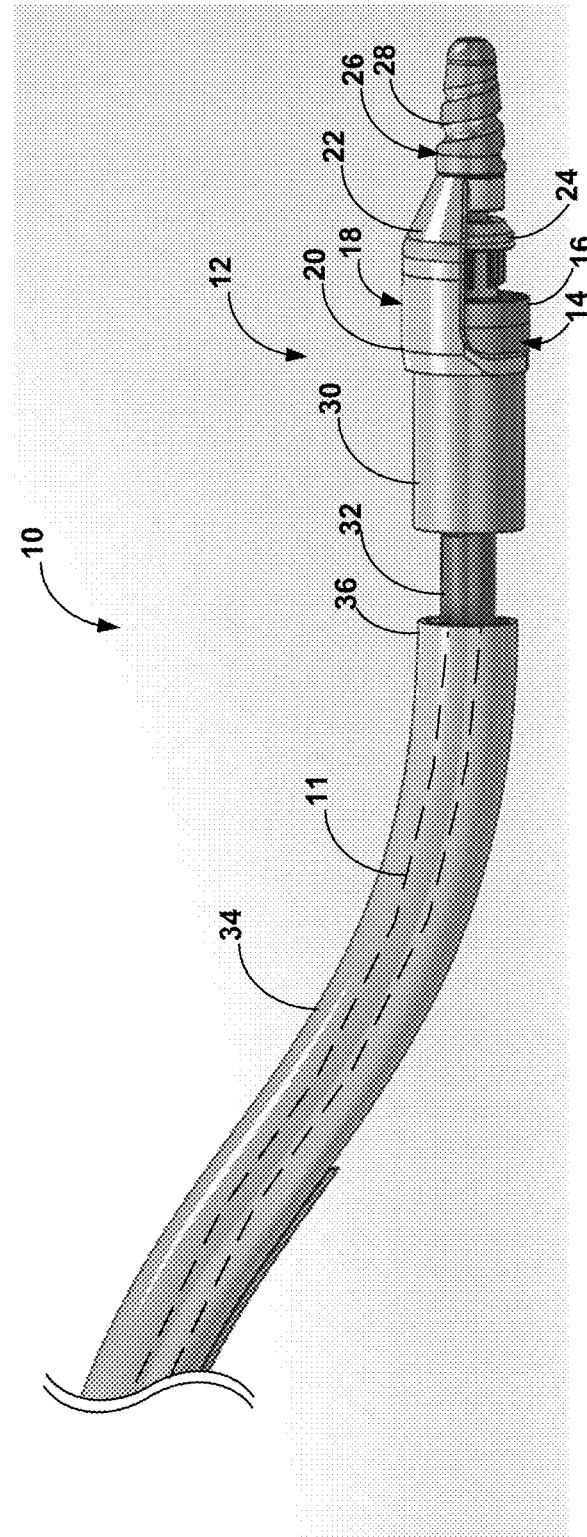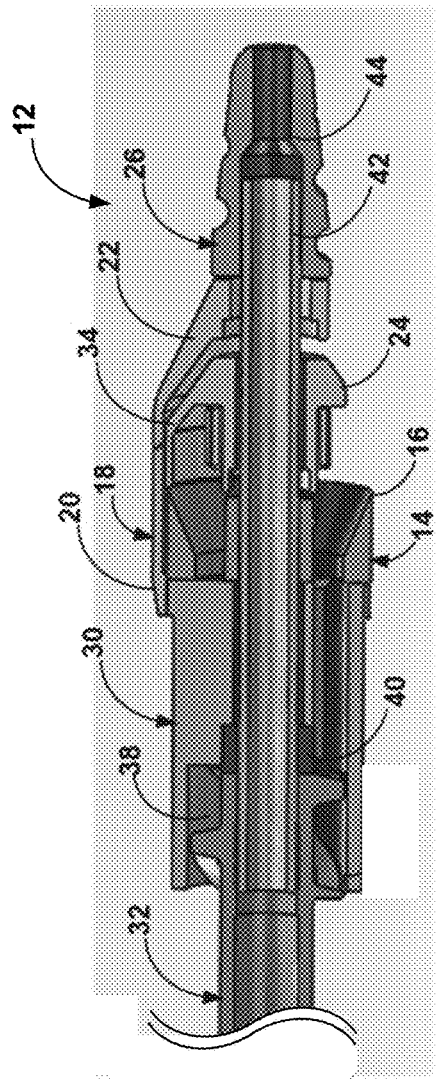
FIG. 1A
FIG. 1B

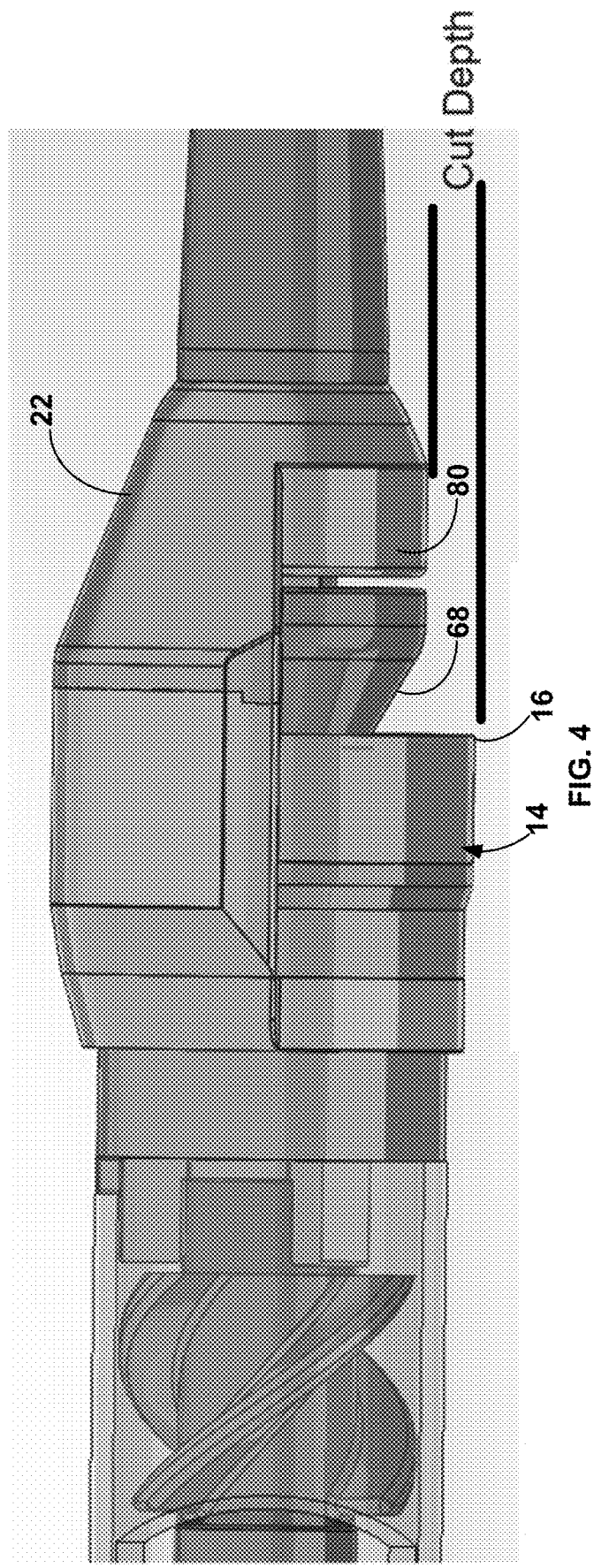

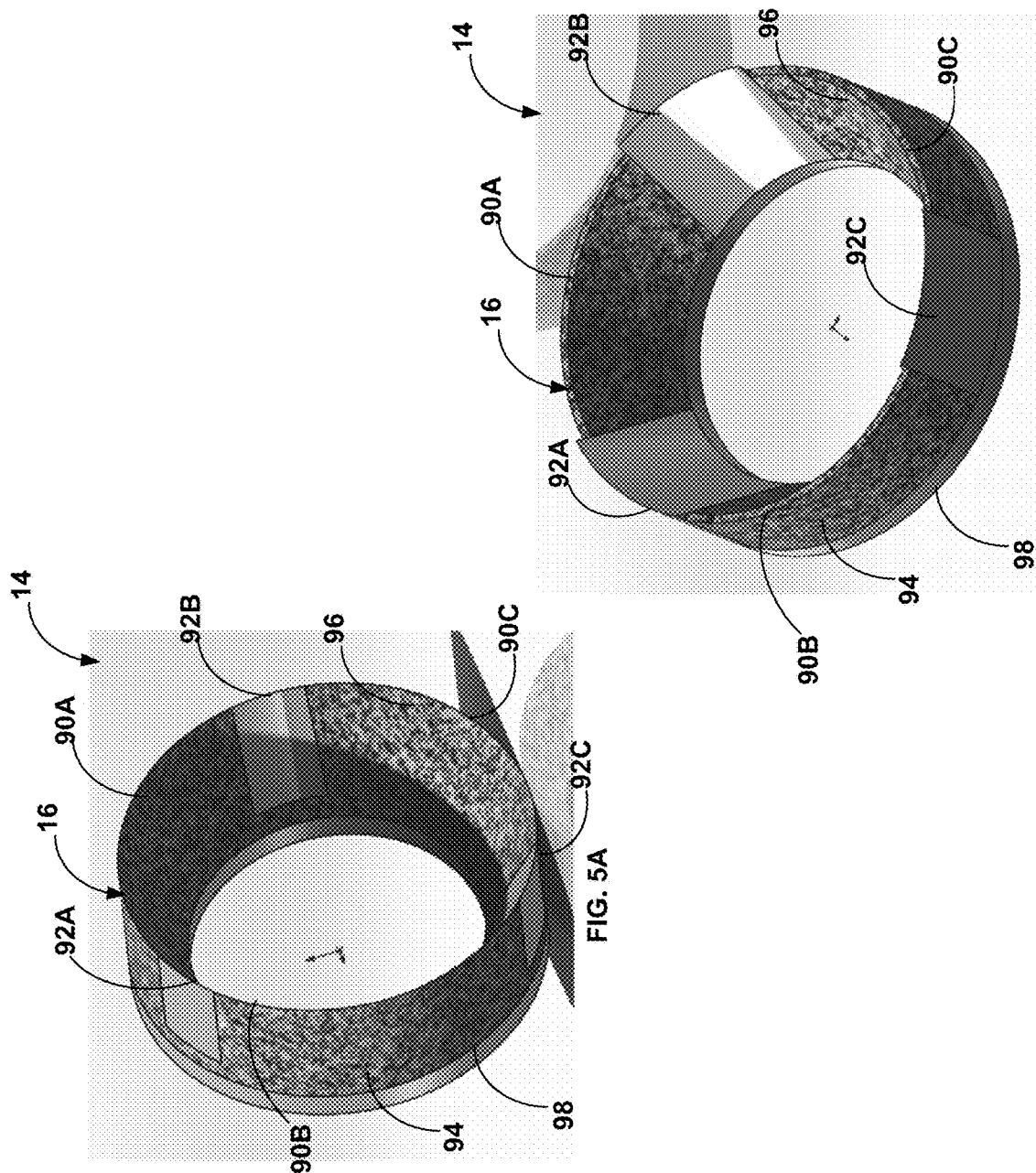

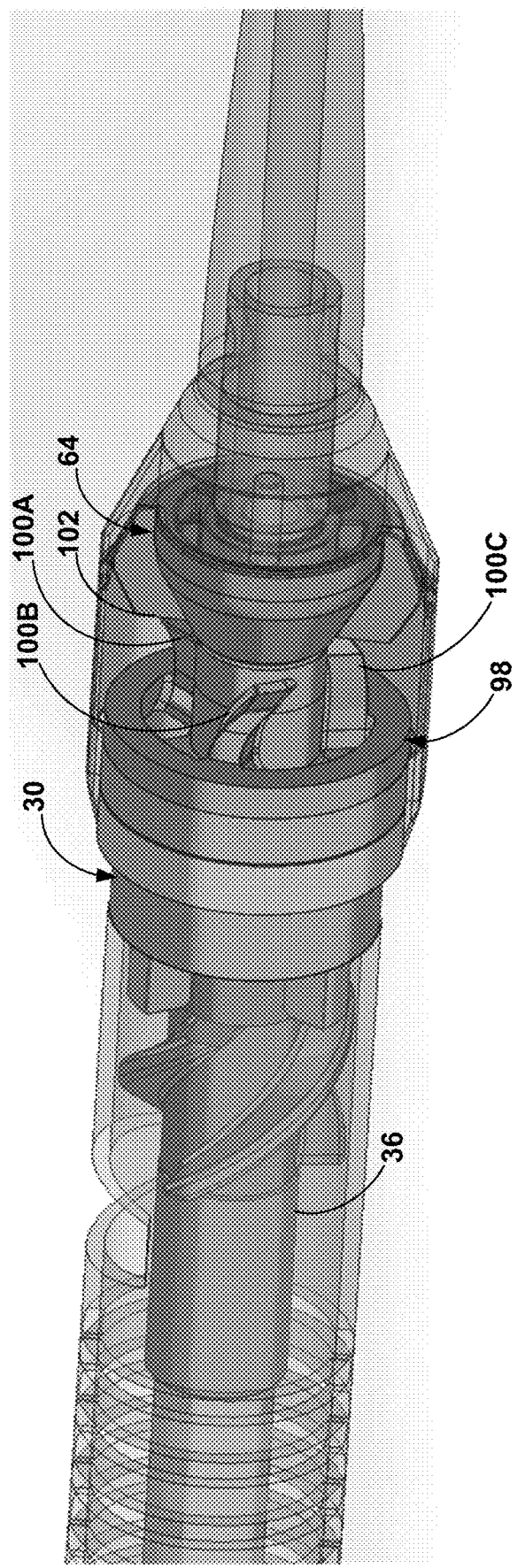

SYSTEM, DEVICE, AND METHOD FOR INTERRUPTED DUAL ACTION (SANDING AND CUTTING) FORCES WITH CONTINUAL MACERATION AND ASPIRATION

CROSS-REFERENCE TO RELATED APPLICATIONS

This application is a divisional of U.S. patent application Ser. No. 16/665,726, filed Oct. 28, 2019 and claims the benefit and priority of U.S. Provisional Patent Application No. 62/752,083, filed Oct. 29, 2018, the contents of which are incorporated herein in their entirety.

STATEMENT REGARDING FEDERALLY SPONSORED RESEARCH OR DEVELOPMENT

Not Applicable

BACKGROUND OF THE INVENTION

Field of the Invention

This invention relates to intravascular procedures generally and more specifically to procedures for removal of plaque or other deposits comprising hard and/or soft materials from a blood vessel with a single cutting and/or abrading element.

Description of the Related Art

Atherectomy is a non-surgical procedure to open blocked coronary arteries or vein grafts by using a device on the end of a catheter to cut or shave away atherosclerotic plaque (a deposit of fat and other substances that accumulate in the lining of the artery wall). For the purposes of this application, the term "abrading" is used to describe the grinding, sanding, and/or scraping action of such an atherectomy head.

Atherectomy uses a rotating shaver or other device placed on the end of a catheter to slice away or destroy plaque. At the beginning of the procedure, medications to control blood pressure, dilate the coronary arteries, and prevent blood clots are administered. The patient is awake but sedated. The catheter is inserted into an artery in the groin, leg, or arm, and threaded through the blood vessels into the blocked artery. The cutting head is positioned against the plaque and activated, and the plaque is ground up or suctioned out.

The types of atherectomy are rotational, directional, and transluminal extraction. Rotational atherectomy uses a high speed rotating shaver to grind up plaque. Directional atherectomy was the first type approved, but is no longer commonly used; it scrapes plaque into an opening in one side of the catheter. Transluminal extraction coronary atherectomy uses a device that cuts plaque off vessel walls and vacuums it into a bottle. It is used to clear bypass grafts.

Performed in a catheterization lab, atherectomy is also called removal of plaque from the arteries. It can be used instead of, or along with, balloon angioplasty. Atherectomy is successful about 95% of the time. Plaque forms again in 20-30% of patients.

Several devices have been disclosed that perform rotational atherectomy. For instance, U.S. Pat. No. 5,360,432, issued on Nov. 1, 1994 to Leonid Shturman, and titled "Abrasive drive shaft device for directional rotational atherectomy" discloses an abrasive drive shaft atherectomy device for removing stenotic tissue from an artery, and is incorporated by reference herein in its entirety. The device includes a rotational atherectomy apparatus having a flexible, elongated drive shaft having a central lumen and a segment, near its distal end, coated with an abrasive material to define an abrasive segment.

For all of these devices, the abrasive head includes an abrasive that has a single set of properties. For instance, an abrasive burr may include abrasive particles of a particular size or a particular distribution of sizes. Or, a particular head may have a cutting effect on the blockage, rather than a grinding effect.

There may be some instances when a practitioner requires two different abrading heads for a single blockage. For instance, a particular blockage may have hard plaques, which may be effectively removed by sanding or scraping, as well as soft lesions, which may be effectively removed by slicing or cutting. The cutting head may have different properties than the scraping head.

A problem with current atherectomy procedures is that it can be difficult to know or predict the exact lesion morphology prior to selecting a specific device to remove the lesion. Also, the current atherectomy devices' methods of action tend to work well in only one type of lesion morphology. For example, if the practitioner expects the lesion to have calcified lesion composition, then he or she may select a removal tool or device that works best to remove hard calcified material or tissue. However, the reality is that many lesions comprise more than one tissue morphology, wherein a single lesion may have both hard (calcified) and softer (fibrotic) tissue.

In known systems, if the practitioner wants to use a first abrasive, then use a second abrasive having different properties than the first abrasive, the practitioner must remove the device with the first abrasive, then insert the device with the second abrasive. This removal of one catheter and insertion of another catheter is time-consuming, inconvenient, expensive, and requires additional parts that must be manufactured, shipped, inventoried, and maintained with the atherectomy device.

Accordingly, an atherectomy device that works well in all, or in a wide range, of lesion types is desirable. Such a head would reduce the expense, time and burden of using additional heads for the rotational atherectomy device.

Further, current atherectomy devices that comprise aspiration functionality must aspirate the same wide range of lesion morphologies; i.e., both harder calcified morphologies and softer fibrotic morphologies. In some current examples, a device may be designed to aspirate harder, smaller particles of calcified tissue, but may not work as well or may clog during aspiration of softer and/or larger chunks of cut fibrotic tissue.

Accordingly, an atherectomy device configured to macerate abraded and/or cut tissue into smaller particles prior to aspiration thereof is desirable. Such a head would improve the functionality of the atherectomy device by reducing clogging during aspiration of cut tissue, thereby improving the efficiency of the procedure.

Further, some current atherectomy devices that comprise a cutting head do not include a feature limiting the depth to which the cutting head can cut tissue. In other current examples, a feature for limiting the cutting depth of the cutting head is included, but in some cases comprises an additional dedicated component that moves the cutting head outwardly or inwardly relative to a longitudinal axis of the device, thereby adding bulk to the device and complicating its operation.

Accordingly, an atherectomy device that provides a passive depth control feature for cutting head without the added bulk and complication of a dedicated component to operate the cutter protector is desirable, such as depth control provided by one or more components of the device that serve other functions. Such a head would reduce the bulk, time and burden of using additional components to control the cutting depth of a cutting head.

Another problem with current atherectomy procedures is that undesired abrasion or dissection of non-lesion tissue can occur if the abrading or cutting head is exposed during tracking and manipulation of the device to the site of a lesion. Some known systems include a movable cover configured to selectively shield the abrading or cutting head to help prevent undesired abrasion or dissection of non-lesion tissue. However, such movable covers typically require an additional component to operate the cutter protector, thereby adding bulk to the device and complicating its operation.

Accordingly, an atherectomy device that provides a passively operable, movable cover for an abrading or cutting head without the added bulk and complication of a dedicated component to operate the cutter protector is desirable. Such a head would reduce the bulk, time and burden of using additional components to selectively cover and uncover an abrading or cutting head.

The present invention addresses, inter alia, these issues.

BRIEF SUMMARY OF THE INVENTION

Various embodiments of a system, device, and method for treating intravascular lesions comprising more than one morphology are provided. Exemplary morphologies may comprise hardened or calcified tissue in combination with softer or fibrotic tissue. Embodiments of the present invention solve this problem by combining more than one method of action into a single device, making the device much more effective than known devices at debulking a wide range of tissue morphologies.

Moreover, embodiments of the present invention solve the above-described issue of handling aspiration of a wide range of lesion morphologies by including a multi-stage macerator that chops up whatever is encountered into consistently sized smaller particles, in a plurality of stages, thereby eliminating clogging so the aspiration flow remains consistent no matter the morphology of the subject tissue.

Additionally, or alternatively, various embodiments of a system, device, and method for treating intravascular lesions with a cutting and/or abrading mechanism are provided. Such embodiments include a rotationally movable guard for the cutting and/or abrading mechanism, the rotationally movable guard being passively operable during rotation of a drive shaft of the device without requiring any additional, dedicated components to actuate the cutter guard.

Additionally, or alternatively, various embodiments of a system, device, and method for treating intravascular lesions with a cutting and/or abrading mechanism are provided. Such embodiments control the depth to which the cutting and/or abrading mechanism can penetrate tissue, the depth control being provided by one or more components of the device that serve other functions without requiring any additional components to move the cutting and/or abrading mechanism.

An embodiment is a rotational device for removing occlusive material within a fluid-filled tubular structure, comprising: a drive shaft configured for insertion into the fluid-filled tubular structure, the drive shaft defining a distal section; a cutter mechanism disposed on the distal section of the drive shaft such that the cutter mechanism rotates when the drive shaft rotates, the cutter mechanism comprising a cutting edge configured to remove occlusive material from within the fluid-filled tubular structure when the drive shaft is rotated and the cutter mechanism is positioned in engagement with the occlusive material; and a cutter mechanism guard disposed on the distal section of the drive shaft, the cutter mechanism guard extending radially outwardly from the cutter mechanism and rotatable between: a first position wherein the cutter mechanism guard surrounds at least a portion of the cutting edge and prevents the cutting edge from engaging the occlusive material; and a second position wherein the cutter mechanism exposes the portion of the cutting edge to enable the cutting edge to engage and remove the occlusive material, wherein rotation of the drive shaft generates friction and vortex flow within the fluid in the fluid-filled tubular structure, and wherein the friction and the vortex flow cause the cutter mechanism guard to rotate between the first position and the second position.

A further embodiment is a rotational device for removing occlusive material within a fluid-filled tubular structure, comprising: a drive shaft configured for insertion into the fluid-filled tubular structure, the drive shaft defining a distal section; a cutter mechanism disposed on the distal section of the drive shaft such that the cutter mechanism rotates when the drive shaft rotates, the cutter mechanism comprising a cutting edge configured to remove occlusive material from a lesion within the fluid-filled tubular structure when the drive shaft is rotated and the cutter mechanism is positioned in engagement with the occlusive material; and a cutter mechanism guard disposed on the distal section of the drive shaft, the cutter mechanism guard extending radially outwardly from the cutter mechanism and rotatable between: a first position wherein the cutter mechanism guard surrounds at least a portion of the cutting edge and prevents the cutting edge from engaging the occlusive material; and a second position wherein the cutter mechanism exposes the portion of the cutting edge to enable the cutting edge to engage and remove the occlusive material, wherein rotation of the drive shaft generates friction and vortex flow within the fluid in the fluid-filled tubular structure, and wherein the friction and the vortex flow cause the cutter mechanism guard to rotate between the first position and the second position.

A further embodiment is a rotational device for removing occlusive material within a fluid-filled tubular structure, comprising: a drive shaft configured for insertion into the fluid-filled tubular structure, the drive shaft defining a distal section; a cutter mechanism disposed on the distal section of the drive shaft such that the cutter mechanism rotates when the drive shaft rotates, the cutter mechanism comprising a cutting edge configured to remove occlusive material from a lesion within the fluid-filled tubular structure when the drive shaft is rotated and the cutter mechanism is positioned in engagement with the occlusive material; and a distal nosecone coupled to the distal section of the drive shaft extending distally of the cutting edge, wherein the distal nosecone defines a tapered profile such that a first outer diameter at a proximal end of the distal nosecone is greater than a second outer diameter at a distal end of the distal nosecone, wherein the distal nosecone is configured to limit the depth to which the cutting edge penetrates the lesion during removal of the occlusive material from the lesion, and wherein the tapered profile of the distal nosecone is configured to draw occlusive material proximally toward the cutting edge as the distal nosecone is advanced along the lesion.

A further embodiment is a rotational device for removing occlusive material within a fluid-filled tubular structure, comprising: a drive shaft configured for insertion into the fluid-filled tubular structure, the drive shaft defining a distal section; a cutter mechanism disposed on the distal section of the drive shaft such that the cutter mechanism rotates when the drive shaft rotates, the cutter mechanism comprising a cutting edge configured to remove occlusive material from a lesion within the fluid-filled tubular structure when the drive shaft is rotated and the cutter mechanism is positioned in engagement with the occlusive material; a cutter shroud coupled to the distal section of the drive shaft, the cutter shroud defining a proximal section surrounding a portion of the cutter mechanism and defining a distal section extending distally of the cutting edge, wherein the distal section of the cutter shroud defines a tapered profile such that a first outer diameter at a proximal end of the distal section of the cutter shroud is greater than a second outer diameter of the distal section of the cutter shroud at a distal end of the distal section of the cutter mechanism, and wherein the distal section of the cutter shroud is configured to limit the depth to which the cutting edge penetrates the lesion during removal of the occlusive material from the lesion; and a cutting-depth control member comprising a distal section of the cutter shroud and an inner cutting-depth control member, wherein the inner cutting-depth control member defines a tapered profile such that a first outer diameter of the inner cutting-depth control member at the cutting edge is less than a second outer diameter of the inner cutting-depth control member distal to the cutting edge, and wherein the tapered profile of the inner cutting-depth control member is configured to control cutting depth and draw occlusive material proximally toward the cutting edge as the inner cutting-depth control member is advanced along the lesion.

A further embodiment is a rotational device for removing occlusive material within a fluid-filled tubular structure, comprising: a drive shaft configured for insertion into the fluid-filled tubular structure, the drive shaft defining a distal section; a cutter mechanism coupled to the distal section of the drive shaft such that the cutter mechanism rotates when the drive shaft rotates, the cutter mechanism comprising: a sharp distal cutting edge configured to cut non-calcified occlusive material from within the fluid-filled tubular structure when the drive shaft is rotated and the sharp distal cutting edge is positioned in engagement with the non-calcified occlusive material; and a major outer surface coated with an abrasive composition and configured to abrade calcified occlusive material from within the fluid-filled tubular structure when the drive shaft is rotated and the abrasive surface of the cutter mechanism is positioned in engagement with the calcified occlusive material.

A further embodiment is a rotational device for removing occlusive material within a fluid-filled tubular structure, comprising: a drive shaft configured for insertion into the fluid-filled tubular structure, the drive shaft defining a distal section; a cutter mechanism coupled to the distal section of the drive shaft such that the cutter mechanism rotates when the drive shaft rotates, the cutter mechanism comprising: a distal cutting edge configured to cut occlusive material from a lesion within the fluid-filled tubular structure when the drive shaft is rotated and the distal cutting edge is positioned in engagement with the occlusive material, wherein the distal cutting edge comprises at least one abrasive section coated with an abrasive composition and at least one sharp section that is not coated with the abrasive composition; and a major outer surface coated with the abrasive composition and configured to abrade calcified occlusive material from within the fluid-filled tubular structure when the drive shaft is rotated and the abrasive surface of the cutter mechanism is positioned in engagement with the calcified occlusive material.

A further embodiment is a rotational device for removing occlusive material within a fluid-filled tubular structure, comprising: a drive shaft configured for insertion into the fluid-filled tubular structure, the drive shaft defining a distal section; a cutter mechanism coupled to the distal section of the drive shaft such that the cutter mechanism rotates when the drive shaft rotates, the cutter mechanism comprising a cutting edge configured to remove occlusive material from a lesion within the fluid-filled tubular structure when the drive shaft is rotated and the cutter mechanism is positioned in engagement with the occlusive material; and a multi-stage macerator configured to macerate occlusive material removed from the lesion, the multi-stage macerator comprising: a first stage coupled to the drive shaft proximal to the cutting edge, the first stage configured to macerate occlusive material removed from the lesion and proximally force the macerated material when the drive shaft is rotated; a second stage coupled to the drive shaft proximal to the first stage, the second stage configured to receive the macerated occlusive material from the first stage, cut the macerated occlusive material into smaller pieces of occlusive material, and proximally force the smaller pieces when the drive shaft is rotated; and a third stage coupled to the drive shaft proximal to the second stage, the third stage configured to receive the smaller pieces of occlusive material from the second stage and cut the smaller pieces of occlusive material into smaller particles of occlusive material when the drive shaft is rotated.

A further embodiment is a rotational device for removing occlusive material within a fluid-filled tubular structure, comprising: a drive shaft configured for insertion into the fluid-filled tubular structure, the drive shaft defining a distal section; a cutter mechanism coupled to the distal section of the drive shaft such that the cutter mechanism rotates when the drive shaft rotates, the cutter mechanism comprising a cutting edge configured to remove occlusive material from a lesion within the fluid-filled tubular structure when the drive shaft is rotated and the cutter mechanism is positioned in engagement with the occlusive material; and a multi-stage macerator configured to macerate occlusive material removed from the lesion, the multi-stage macerator comprising: a first stage coupled to the drive shaft proximal to the cutting edge, the first stage configured to macerate occlusive material removed from the lesion and proximally force the macerated material when the drive shaft is rotated; a second stage coupled to the drive shaft proximal to the first stage, the second stage configured to receive the macerated occlusive material from the first stage, cut the macerated occlusive material into smaller pieces of occlusive material, and proximally force the smaller pieces when the drive shaft is rotated; and a third stage coupled to the drive shaft proximal to the second stage, the third stage configured to receive the smaller pieces of occlusive material from the second stage and cut the smaller pieces of occlusive material into smaller particles of occlusive material when the drive shaft is rotated.

Moreover, we provide disclosure of the following patents and applications, each of which are assigned to Cardiovascular Systems, Inc., and incorporated herein in their entirety, each of which may comprise systems, methods and/or devices that may be used with various embodiments of the presently disclosed subject matter:

U.S. Pat. No. 9,468,457, "ATHERECTOMY DEVICE WITH ECCENTRIC CROWN;
U.S. Pat. No. 9,439,674, "ROTATIONAL ATHERECTOMY DEVICE WITH EXCHANGEABLE DRIVE SHAFT AND MESHING GEARS;
U.S. Pat. No. 9,220,529, "ROTATIONAL ATHERECTOMY DEVICE WITH ELECTRIC MOTOR";
U.S. Pat. No. 9,119,661, "ROTATIONAL ATHERECTOMY DEVICE WITH ELECTRIC MOTOR;
U.S. Pat. No. 9,119,660, "ROTATIONAL ATHERECTOMY DEVICE WITH ELECTRIC MOTOR";
U.S. Pat. No. 9,078,692, "ROTATIONAL ATHERECTOMY SYSTEM";
U.S. Pat. No. 6,295,712, "ROTATIONAL ATHERECTOMY DEVICE";
U.S. Pat. No. 6,494,890, "ECCENTRIC ROTATIONAL ATHERECTOMY DEVICE;
U.S. Pat. No. 6,132,444, "ECCENTRIC DRIVE SHAFT FOR ATHERECTOMY DEVICE AND METHOD FOR MANUFACTURE;
U.S. Pat. No. 6,638,288, "ECCENTRIC DRIVE SHAFT FOR ATHERECTOMY DEVICE AND METHOD FOR MANUFACTURE";
U.S. Pat. No. 5,314,438, "ABRASIVE DRIVE SHAFT DEVICE FOR ROTATIONAL ATHERECTOMY";
U.S. Pat. No. 6,217,595, "ROTATIONAL ATHERECTOMY DEVICE";
U.S. Pat. No. 5,554,163, "ATHERECTOMY DEVICE";
U.S. Pat. No. 7,507,245, "ROTATIONAL ANGIOPLASTY DEVICE WITH ABRASIVE CROWN";
U.S. Pat. No. 6,129,734, "ROTATIONAL ATHERECTOMY DEVICE WITH RADIALLY EXPANDABLE PRIME MOVER COUPLING;
U.S. patent application Ser. No. 11/761,128, "ECCENTRIC ABRADING HEAD FOR HIGH-SPEED ROTATIONAL ATHERECTOMY DEVICES";
U.S. patent application Ser. No. 11/767,725, "SYSTEM, APPARATUS AND METHOD FOR OPENING AN OCCLUDED LESION";
U.S. patent application Ser. No. 12/130,083, "ECCENTRIC ABRADING ELEMENT FOR HIGH-SPEED ROTATIONAL ATHERECTOMY DEVICES";
U.S. patent application Ser. No. 12/363,914, "MULTI-MATERIAL ABRADING HEAD FOR ATHERECTOMY DEVICES HAVING LATERALLY DISPLACED CENTER OF MASS";
U.S. patent application Ser. No. 12/578,222, "ROTATIONAL ATHERECTOMY DEVICE WITH PRE-CURVED DRIVE SHAFT";
U.S. patent application Ser. No. 12/130,024, "ECCENTRIC ABRADING AND CUTTING HEAD FOR HIGH-SPEED ROTATIONAL ATHERECTOMY DEVICES";
U.S. patent application Ser. No. 12/580,590, "ECCENTRIC ABRADING AND CUTTING HEAD FOR HIGH-SPEED ROTATIONAL ATHERECTOMY DEVICES";
U.S. patent application Ser. No. 29/298,320, "ROTATIONAL ATHERECTOMY ABRASIVE CROWN";
U.S. patent application Ser. No. 29/297,122, ROTATIONAL ATHERECTOMY ABRASIVE CROWN";
U.S. patent application Ser. No. 12/466,130, "BIDIRECTIONAL EXPANDABLE HEAD FOR ROTATIONAL ATHERECTOMY DEVICE"; and
U.S. patent application Ser. No. 12/388,703, "ROTATIONAL ATHERECTOMY SEGMENTED ABRADING HEAD AND METHOD TO IMPROVE ABRADING EFFICIENCY".

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

BRIEF DESCRIPTION OF THE SEVERAL VIEWS OF THE DRAWINGS

FIG. 1A is a side elevation drawing of a rotational device in accordance with this disclosure.

FIG. 1B is a longitudinal cross-section of a distal cutting section of the rotational device of FIG. 1A.

FIG. 4 is a side elevation drawing of the rotational device of FIG. 2A with the movable cutter guard of the rotational device in an open position, illustrating a cut depth provided by components of the rotational device.

FIGS. 5A and 5B are perspective drawings of embodiments of a cutter mechanism in accordance with this disclosure.

FIG. 6 is a partial-cutaway drawing of the rotational device of FIG. 2A with a proximal section of the cutter shroud and the cutting ring removed to illustrate the teeth of a base of the cutter mechanism.

DETAILED DESCRIPTION OF THE INVENTION

Figure 2A:
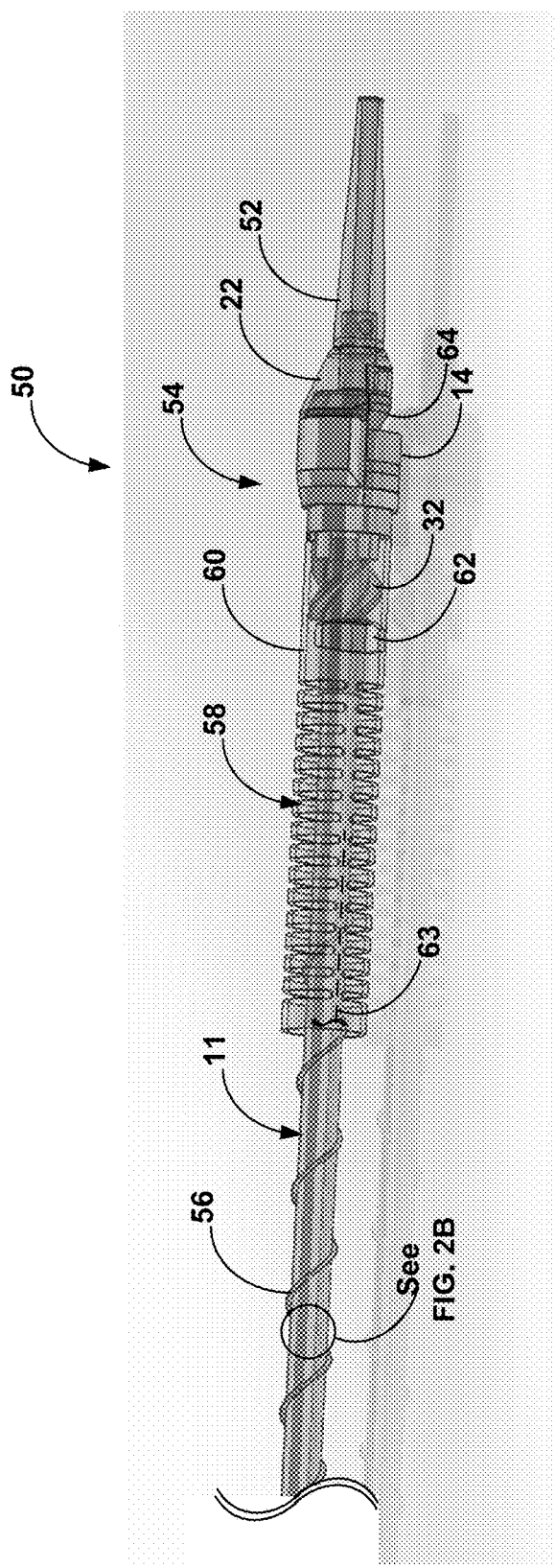
FIG. 2A is a perspective drawing of another rotational device in accordance with this disclosure with a movable cutter guard of the rotational device in an open position.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention. It further should be understood that although one or more of the embodiments described herein are described or illustrated as including each of a multi-stage macerator, a cutter mechanism having dual interrupted cutting and sanding features, a passively-activated rotational cutter guard, and a cutting depth-control, embodiments comprising fewer than all of these four features are also contemplated and within the scope of this disclosure.

The invention generally may be constructed from a combination of various materials. Such materials may include one or more metals, plastics, ceramics, and/or diamond coatings as required. Components of the devices described herein that perform maceration and cutting are formed from materials having sufficient hardness to chop higher density lesion morphologies, including extreme lesion morphologies that may have a hardness similar to bone. Some components of the devices described herein may be heat treated to hold an edge during use. In examples in which ceramic or metal components are included in the devices described herein, such components may be machined, forged or formed from billet or bar stock, or other processes such as metal injection molding, laser sintering, direct metal molding, or any other suitable process. It should be understood that materials and manufacturing processes described with respect to the devices and systems of this disclosure are exemplary in nature and non-limiting, as other suitable rigid or semi-rigid materials and processes may be used in the manufacture of the devices and systems described herein.

FIG. 1A is a side elevation drawing of an example rotational device 10 in accordance with this disclosure. Rotational device 10 may be configured for use within a fluid-filled tubular structure, such as a blood vessel of a patient in which occlusive material is located. In such examples the device 10 is a rotational atherectomy device configured to cut and remove occlusive material from the vasculature of the patient. Numerous features of the device 10 shown in FIG. 1A are introduced here in the context of FIG. 1A and will be discussed in greater detail with respect to later features. Device 10 includes a drive shaft 11 (shown in phantom) and a distal tissue removal section 12 disposed on a distal section of the drive shaft 11. The distal tissue removal section 12 includes a cutter mechanism 14 that is configured to cut and/or abrade tissue from a lesion within vasculature of a patient, the cutter mechanism 14 having a substantially cylindrical shape and comprising a distally-facing cutting edge 16. Cutter mechanism 14 is advantageously configured to provide dual interrupted cutting and sanding functions that enable cutter mechanism 14 to cut and/or abrade both softer fibrotic tissue and harder calcified tissue, as will be discussed in greater detail below with respect to FIGS. 5A-6.

Distal tissue removal section 12 of the device 10 further includes a cutter shroud 18 fixedly coupled to the distal section of the drive shaft 11. The cutter shroud 18 defines a proximal section 20 that surrounds a portion of the cutter mechanism 14 and a distal section 22 that extends distally of the cutting edge. In some embodiments, cutter shroud 18 may be fixedly coupled to the distal end of the drive shaft 11. As illustrated in FIG. 1A, distal section 22 of the cutter shroud 18 defines a tapered profile from its proximal end to its distal end, such that a first outer diameter at a proximal end of the distal section of the cutter shroud is greater than a second outer diameter of the distal section of the cutter shroud at a distal end of the distal section of the cutter. In some examples, the tapered profile of the distal section 22 may define a partial nosecone that helps limit the depth to which the cutting edge 16 can penetrate tissue, alone or in combination with one or more other features of the device 10. Cutter shroud 18 advantageously may be configured to protect non-target areas of patient vasculature from unintentional cutting by cutter mechanism 14 while device 10 is being manipulated within patient vasculature and/or actively cutting tissue.

Distal tissue removal section 12 of the device 10 further includes a rotationally movable cutter mechanism guard 24, the latter of which may be referred to herein as "cutter guard 24" for the sake of brevity. Cutter guard 24 is disposed on the distal section of the drive shaft 11, positioned radially inward of the cutter shroud 18 and surrounding at least a portion of cutter mechanism 14 that includes cutting edge 16. Cutter guard 24 is rotatable between a first (i.e., closed) position and a second (i.e., open) position. When in the first position, the cutter guard 24 surrounds at least a portion of the cutting edge 16 that is not surrounded by cutter shroud 18 and prevents the cutting edge 16 from engaging the occlusive material or other tissue, such as when the cutter mechanism 14 is not being used to debulk a lesion. When in the second position, the cutter guard 24 exposes the portion of the cutting edge 16 to enable the cutting edge 16 to engage and remove occlusive material from the lesion. Thus, when the cutter guard 24 is in the second position, a portion of the cutter mechanism 14 is exposed and usable to debulk a lesion when the drive shaft 11 and the cutter mechanism 14 are rotated. Cutter guard 24, as well as other embodiments of cutter guards described herein, are advantageously configured to be rotationally movable between the closed and open positions without reliance on any direct mechanical linkage to other components of the atherectomy device, as will be discussed in greater detail below with respect to FIGS. 3A and 3B.

Distal tissue removal section 12 of the device 10 further includes a distal tip 26 coupled to the distal section of the drive shaft 11 and forming the distal-most end of device 10. In the embodiment illustrated in FIG. 1A, distal tip 26 comprises an optional abrasive surface 28. The abrasive surface 28 may comprise a diamond coating on the distal tip 26. In examples in which the distal tip 26 includes the abrasive surface 28, the distal tip 26 comprises a tapered front cutter for the device 10 that is positioned about 2-4 millimeters (mm) distally of the distal cutting edge 16. In this manner, the abrasive distal tip 26 may abrade occlusive material from a lesion to open a pilot pathway through the occlusive material ahead of cutter mechanism 14, which may be advantageous in some situations such as chronic total occlusions (CTOs) or near-CTOs in which the vessel is completely blocked or nearly-completely blocked by the occlusive material. The tapered shape and/or size of the distal tip 26 may, in some examples, limit the cutting angle of the cutter mechanism 14, which may help reduce the likelihood of causing an undesired dissection of patient vascular tissue. In other examples, the device 10 may include a distal tip that is flexible and/or non-abrasive.

Distal tissue removal section 12 of the device 10 further includes a macerator body 30 coupled to and surrounding a portion of the distal section of the drive shaft 11 proximal to the cutter mechanism 14, and an impeller 32 comprising at least one cutting edge coupled to the drive shaft 11 proximal to the macerator body 30. The macerator body 30 comprises features that are configured for multi-stage maceration of occlusive material removed from the lesion by the cutter mechanism 14. For example, the macerator body 30 may comprise features configured to receive pre-macerated occlusive material from the cutter mechanism 14, cut the pre-macerated occlusive material into smaller pieces of occlusive material, and proximally force the smaller pieces toward a rear portion of the macerator body 30 that further macerates the smaller pieces of occlusive tissue between the rear portion of the macerator body and the impeller 32 when the drive shaft 11 is rotated. Multi-stage maceration by the embodiments of this disclosure, as well as the macerator body 30 and the impeller 32, are discussed below in greater detail with respect to FIGS. 6-11.

Device 10 additionally includes a flexible elongate sheath 34 surrounding the drive shaft 11 proximal to the impeller 32. The flexible elongate sheath defines a distal end 36 from which the impeller 32 and the rest of the distal tissue removal section 12 extends. The flexible elongate sheath 34 may provide one or more advantages, such as steering capabilities of the device 10 as well as a lumen through which macerated occlusive material may be drawn proximally and out of the patient's vasculature. For example, the flexible elongate sheath 34 may include at least one pull wire (not shown), which may be embedded in a wall of the flexible elongate sheath 34. These features of the flexible elongate sheath 34 are discussed below in greater detail with respect to FIGS. 13A-17.

FIG. 1B is a longitudinal cross-section of the distal tissue removal section 12 of the rotational device 10 of FIG. 1A. Several additional features of the device 10 are visible in the cross-sectional view of FIG. 1B. As shown in FIG. 1B, the macerator body 30 defines a macerator body lumen 38, in which a distal portion of the impeller 32 is received. Device 10 further includes a bushing 40 positioned between the impeller 32 and the macerator body 30, a drive shaft hypotube 42 comprising the distal section of the drive shaft 11, and an inner distal tip 44 coupled to a distal end defined by the drive shaft hypotube 42. In some examples the drive shaft hypotube 42 may be welded to the impeller 32. The bushing 40 may comprise polyether ether ketone (PEEK) or another polymer or other suitable material. The drive shaft hypotube 42 and inner distal tip 44 may comprise any suitable material known in the art.

In the example illustrated in FIGS. 1A and 1B, device 10 is a rotational atherectomy device that enables the cutting, abrading, and removal of occlusive material from a lesion within a patient's vasculature. However, the device 10 should not be understood as being strictly limited to this use. In addition, it should be noted that device 10 is not necessarily limited to treatment of a human patient. In alternative examples, the device 10 may be adapted for use in non-human patients, e.g., primates, canines, equines, pigs, ovines, bovines, and felines. These other animals may undergo clinical or research therapies that may benefit from the subject matter of this disclosure.

FIGS. 2A-13 illustrate a rotational device 50 in accordance with this disclosure. The features of the rotational device 50 are introduced in FIGS. 2A-2D. Additional details of the features of the rotational device 50 and their functions are described with respect to FIGS. 3-13. It should be noted that any one or more of the features, functions, and advantages described herein with respect to the rotational device 50 may be included in the device 10 of FIGS. 1A and 1B and vice versa. It also should be noted that like reference numerals denote substantially-like features across rotational device 10 and rotational device 50; e.g., the cutter mechanism 14 may be substantially the same in rotational device 10 and rotational device 50.

FIG. 2A is a perspective drawing of the rotational device 50 with a rotatably movable cutter guard 64 of the rotational device 50 in an open position. As with the rotational device 10, rotational device 50 also may be configured for use within a fluid-filled tubular structure such as a blood vessel of a patient and comprises a distal tissue removal section 54 similar to the distal tissue removal section 12 of the device 10. In such examples the device 50 is a rotational atherectomy device configured to cut and remove occlusive material from the vasculature of the patient. In one non-limiting example, the distal tissue removal section 54 may have an outer diameter of about 7 French and may be configured for tracking over a 0.014" guide wire. Additionally, or alternatively, the device 50 may be configured in a non-limiting example to provide a 0.25 mm cut depth and/or may be operable at a rotational speed of about 60K rpm. Such values are exemplary and may be adapted to different applications.

As shown in FIG. 2A, the device 50 may include a slotted tube 58 defining a distal section 60 that is configured to clock or orient the distal tip 52 and the cutter mechanism 14 to a spine of slotted tube 58. The slotted tube 58 is positioned proximal to the distal tissue removal section 54 and may be a distal section of the flexible elongate sheath 34, more-proximal sections of which are not shown in FIG. 2A for clarity. In the illustrated example, the distal section 60 of the slotted tube 58 defines one or more visibility windows 62. The visibility window(s) 62 facilitate imaging of one or more features of the device 50 during use, such as a proximal section of impeller 32 past which occlusive material will flow after it is macerated.

The slotted tube 58 comprises a segmented variable stiffness section (e.g. a laser-cut, multi durometer tube) which allows for flex bias in a single plane, keeping the distal tissue removal section 54 opposed to a section of flexible elongate sheath 34 that is proximal to slotted tube 58. Thus, slotted tube 58 comprises a deflection section of the flexible elongate sheath 34. Slotted tube 58 is configured to change shape from a linear configuration to an S-shaped configuration having a curvature similar to the curvature of the flexible elongate sheath 34 illustrated in FIG. 1A. When an operator pulls on a trigger of a handle assembly (illustrated and described with respect to FIGS. 14-17) coupled to a proximal end of the device 50, the trigger then pulls a pull wire 63 that is attached about midway in the slotted tube 58, causing slotted tube 58 to deflect from the linear shape into the S-shape. The pull wire 63 extends proximally through the proximal section of the flexible elongate sheath 34 that is not shown in FIG. 2A. The slotted tube 58 is covered and its slots may be filled with a low durometer polymer that seals the open slots, thereby creating a lumen and acting as springs that return the slotted tube 58 to the linear condition when the pull wire 63 is released.

As illustrated in FIG. 2A, the drive shaft 11 may include a helix-wound wire 56 extending circumferentially around at least a portion of an outer diameter of the drive shaft 11, such as a longitudinally-extending portion of the drive shaft 11 that extends proximally of the impeller 32, and within a lumen defined by the flexible elongate sheath (e.g., elongate sheath 34).

The helix-wound wire 56 is configured to force fluid and occlusive material removed from a lesion by the cutter mechanism 14 proximally through the flexible elongate sheath when the cutter mechanism 14 is rotated within the vasculature and in contact with a lesion. Thus, the helix-wound wire 56 functions as an auger that forces or pumps macerated lesion slurry proximally through the flexible elongate sheath and out of the patient's body, such as to a collection bag coupled to the device 50. This removal of the lesion slurry from the flexible elongate sheath by rotation of the drive shaft 11 and the helix-wound wire 56 advantageously enables the device 50 to treat relatively long lesion lengths without stopping to remove lesion material.

The helix-wound wire 56 may be coupled to the drive shaft 11 by any suitable means. For example, the helix-wound wire 56 may be soldered, welded, adhered, or otherwise coupled to the drive shaft 11. The helix-wound wire 56 also may vary in pitch, with the following examples being non-limiting: 0.083"/52 degrees; 0.099"/48 degrees; 0.109"/48 degrees; or 0.143"/38 degrees. Examples of achievable passive flow rates provided by these example pitches are shown below in Table 1 for different drive shaft speeds using 35% glycerol:

TABLE 1

Passive Aspiration

| | Flow Rate (ml/min) | | |
|---|---|---|---|
| Auger Pitch | 60,000 rpm (250) | 70,000 rpm (292) | 80,000 rpm (333) |
| 0.083" | 33.5 | 44.2 | 53 |
| 0.099" | 41.2 | 51 | 60 |
| 0.109" | 43.5 | 51.2 | 61 |
| 0.143" | 42.3 | 50.1 | 59 |

In some examples, a system comprising the device 50 optionally provides powered vacuum-assisted aspiration via a powered pump. With respect to such examples, achievable active flow rates provided at different powered-pump speeds are shown below in Table 2 using 35% glycerol:

TABLE 2

Active Aspiration

| Pump Speed | Flow Rate (ml/min) |
|---|---|
| 90 | 24.3 |
| 80 | 31.5 |
| 70 | 37.7 |
| 60 | 35.4 |
| 49.56 | 33.6 |

Figure 2B:
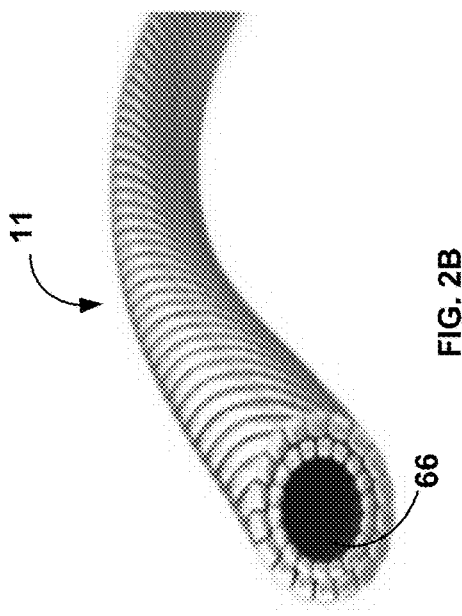
FIG. 2B is a perspective drawing of the section of drive shaft circled in FIG. 2A.

FIG. 2B is a perspective drawing of the section of drive shaft 11 circled in FIG. 2A. As illustrated in FIG. 2B, the drive shaft 11 may be a multi-layer helical hollow strand (HHS) drive shaft that defines an inner lumen 66 trackable over a suitable guide wire (not shown). However, other suitable drive shaft configurations may be used with the helix-wound wire 56. The features of device 50 described above may be included in device 10 of FIGS. 1A and 1B.

The following features of device 50 may be used interchangeably with corresponding features of device 10 illustrated in FIGS. 1A and 1B and described with respect thereto. For example, device 50 includes a flexible, non-abrasive distal tip 52 coupled to the distal end of the drive shaft 11 instead of the abrasive distal tip 26. The flexible, non-abrasive distal tip 52 may help improve tracking of device 50 over a guide wire. In some examples, the distal tip 52 may be hollow. Distal tip 52 may be produced from multiple (e.g., 14) parts, a plurality of which may be produced using micro laser sintering. In one non-limiting example, the distal tip 52 may have a rigid length of about 8.25 mm with a minimum wall thickness of about 100 microns. The device 50 further includes a rotatably movable cutter guard 64, better illustrated and described below with respect to the cross-section of FIG. 2C. Similarly to the cutter guard 24 of the device 10, the rotatably movable cutter guard 64 is disposed on the distal section of the drive shaft 11 and extends radially outwardly therefrom.

Figure 2C:
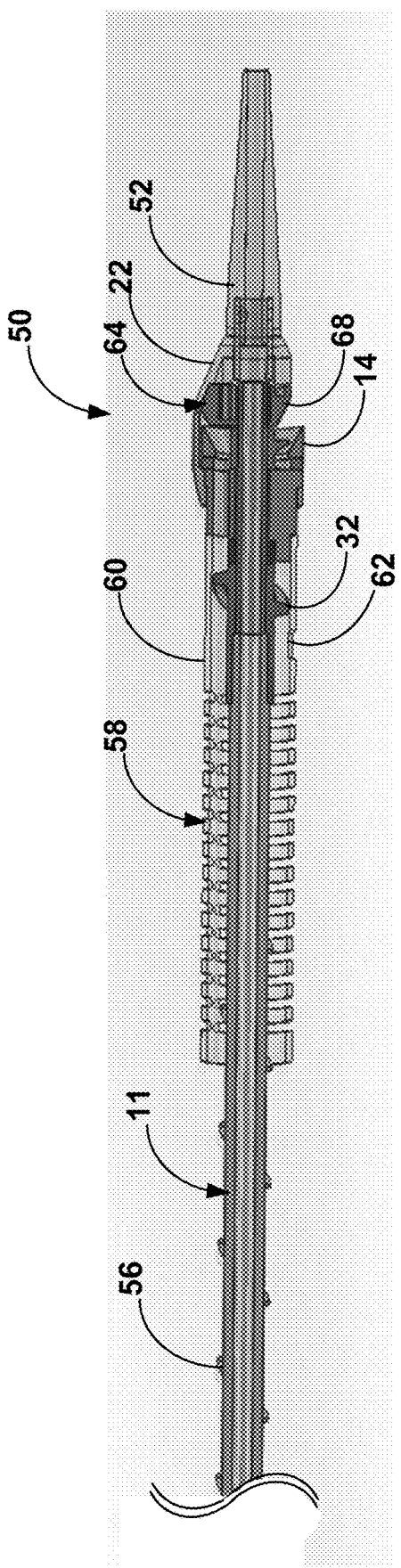
FIG. 2C is a longitudinal cross-section of a distal cutting section of the rotational device of FIG. 2A.

FIG. 2C is a longitudinal cross-section of a distal tissue removal section 54 of the rotational device 50 of FIG. 2A. FIG. 2C illustrates that the rotatably movable cutter guard 64 has a different configuration than the configuration of the cutter guard 24 of the device 10. Specifically, with the cutter guard 64 in the open configuration shown in FIG. 2C, a lower portion 68 of cutter guard 64 that is opposite the fixed cutter shroud 18 (i.e., relative to a longitudinal axis of drive shaft 11) presents a tapered profile. This tapered profile of the lower portion 68 of the cutter guard 64 is configured to draw occlusive material proximally toward cutting edge 16 as the lower portion 68 of the cutter guard 64 is advanced along a lesion.

Figure 2D:
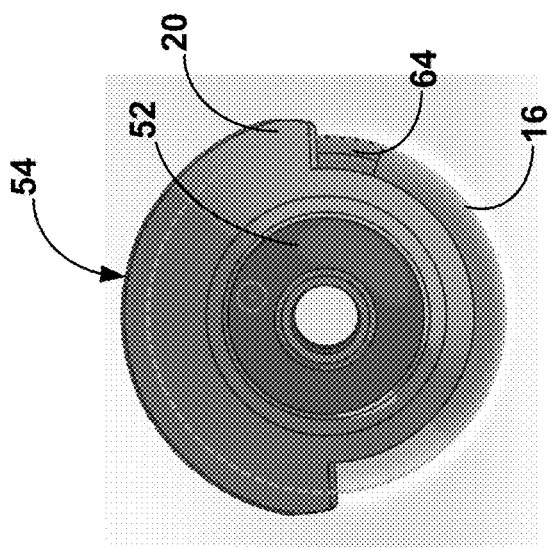
FIG. 2D is a front elevation drawing of the rotational device of FIG. 2A.

FIG. 2D is a front elevation drawing of the rotational device of FIG. 2A. FIG. 2D illustrates that proximal section 20 of the cutter shroud 18 extends only partially around cutter mechanism 14. That is, the device 50 does not have material of the cutter shroud 18 proximally of the cutting edge 16 in the lower half of the distal tissue removal section 54. This configuration advantageously may enable the cutter mechanism 14 to pass through tougher lesions without the occlusive material binding on the cutter shroud 18.

Figure 3A:
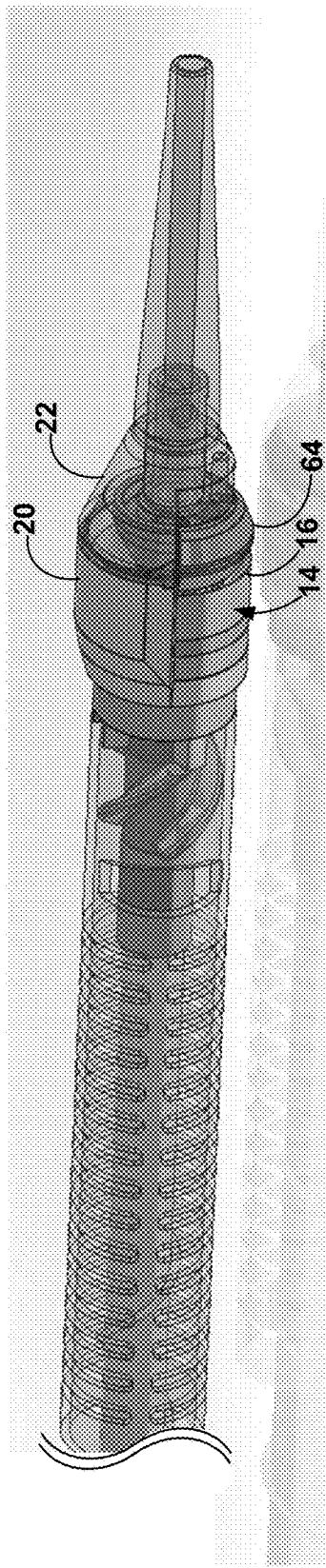
FIG. 3A is a longitudinal perspective drawing of the rotational device of FIG. 2A illustrating the movable cutter guard in a closed position.

FIG. 3A is a longitudinal perspective drawing of the rotational device of FIG. 2A illustrating the movable cutter guard in a closed position. As with the cutter guard 24 of the device 10, the cutter guard 64 also is rotatable between a first (i.e., closed) position and a second (i.e., open) position. When in the first position, the cutter guard 64 likewise surrounds at least a portion of the cutting edge 16 that is not surrounded by cutter shroud 18 and prevents the cutting edge 16 from engaging the occlusive material or other tissue, such as when the cutter mechanism 14 is not being used to debulk a lesion. When in the second position, the cutter guard 64 likewise exposes the portion of the cutting edge 16 to enable the cutting edge 16 to engage and remove occlusive material from the lesion. Thus, when the cutter guard 64 is in the second position, a portion of the cutter mechanism 14 is exposed and usable to debulk a lesion when the drive shaft 11 and the cutter mechanism 14 are rotated.

Advantageously, the cutter guard 64 is rotationally movable between the closed and open positions without reliance on any direct mechanical linkage to other components of the device 50 and without requiring any additional, dedicated components to actuate the cutter guard 64. Instead, the cutter guard 64 is rotationally movable between the closed and open positions via a combination of friction and vortex flow (i.e., of fluid within the patient's vasculature). In some contemplated examples, when the drive shaft 11 rotates in the "cut" direction, friction and directional vortex flow cause the cutter guard to rotate (e.g., about 180 degrees) from the closed position to the open position without any additional user input. When a prime mover powering the drive shaft 11 is turned off, the drive shaft 11 reverses direction for a preset time at a low speed to generate friction and vortex flow in the opposite direction, thereby moving the cutter guard 64 from the open position to the closed position without any additional user input. In this manner, the cutter guard 64 is movable without reliance on direct mechanical linkage to other components of the device 50, thus avoiding the bulk of additional components that otherwise would be needed to operate a movable cutter guard and allowing the device 50 to have a smaller profile.

Figure 3B:
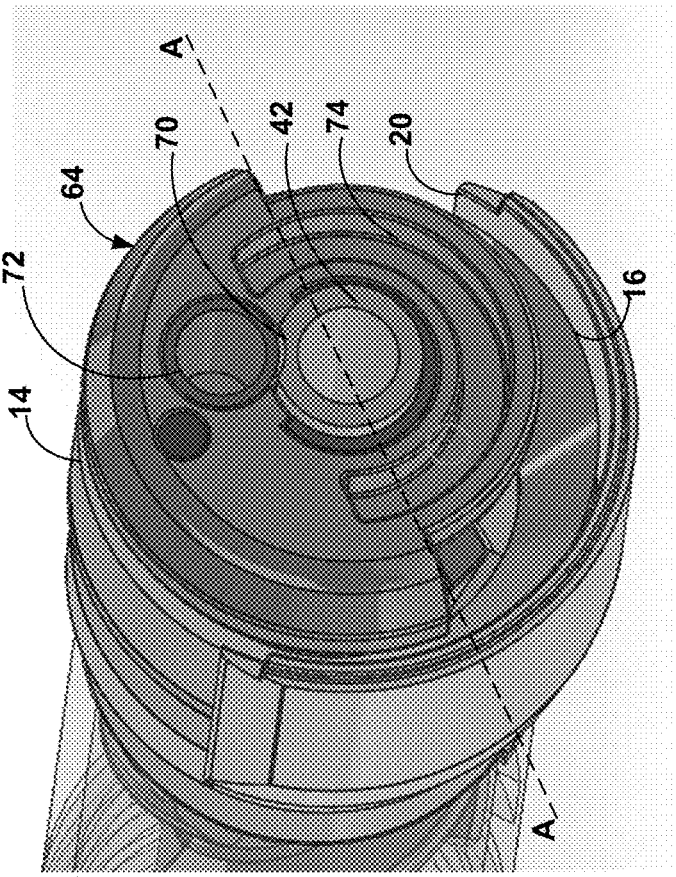
FIG. 3B is a partial-cutaway drawing of the rotational device of FIG. 2A with a distal tip and a distal section of a cutter shroud removed to illustrate the movable cutter guard.

FIG. 3B is a partial-cutaway drawing of the rotational device of FIG. 2A with the distal tip 52 and the distal section 22 of the cutter shroud 18 removed to further illustrate the rotatably movable cutter guard 64. As can be seen in FIGS. 3A and 3B, the cutter guard 64 has a substantially frustoconical shape that can be divided longitudinally into two sections along plane A, with a longitudinal section on a first side of Plane A having smaller dimensions than a longitudinal section on a second side of Plane A. This aspect of the configuration of the cutter guard 64 enables the cutter guard to cover or expose the cutting edge 16 depending on the direction in which the cutter guard 64 is rotated.

During use, rotation of the drive shaft 11 causes rotation of the cutter guard 64. When the cutter guard is rotated from the closed position to the open position, a notch 70 defined by the drive shaft hypotube 42 engages a small tube 72 that rotates the cutter guard 64. The distal section 22 of the cutter shroud 18 (not shown in FIG. 3B) includes a tang that fits within a curved slot 74 defined by the cutter guard 64 and limits the cutter guard rotation to 180 degrees so that the cutter guard remains in the open position or closed position as desired.

FIG. 4 is a side elevation drawing of the rotational device of FIG. 2A with the movable cutter guard 64 of the rotational device 50 in the open position, illustrating a cut depth provided by components of the rotational device 50. Control of the cutting depth of the cutter mechanism 14 is provided by an inner portion 80 of the distal section 22 of the cutter shroud 18 and the lower portion 68 of the cutter guard 64. The size of the gap between the inner portion 80 of the distal section 22 of the cutter shroud 18 and the cutting edge 16 defines the cut depth. During use, a user deflects a distal tip of the flexible elongate sheath (e.g., sheath 34) to one side targeting occlusive lesion material. Even if the user over deflects the tip, the inner portion 80 of the distal section 22 of the cutter shroud 18 still limits the cut depth of the cutter mechanism 14. In this manner, the features of the distal tissue removal section 54 of the device 50 enable a consistent cut depth to be maintained regardless of the deflection distance, deflection force and tip approach angle of the distal tissue removal section 54 relative to the occlusive material. For example, approach angles up to about a 15 degree approach angle create the same cut depth. This feature enables efficient and predictable cutting of occlusive material while helping reduce the likelihood of undesirable tissue dissection.

FIGS. 5A and 5B are perspective drawings of embodiments of cutter mechanism 14 in accordance with this disclosure. It should be noted that at least in the context of the embodiments of FIGS. 5A and 5B, the "cutting edge" 16 should be understood to include both cutting and sanding/abrading sections as described herein. As shown in FIGS. 5A and 5B, the cutter mechanism 14 may comprise a interrupted cutting and sanding configuration wherein the outer and inner surfaces of the cutter mechanism 14 have alternating sharp sections 92A, 92B, 92C and abrasive sections 90A, 90B, 90C that extend around the perimeter of the cutter mechanism 14 at the cutting edge 16, and extending at least partially longitudinally away from the cutting edge 16 of the cutter mechanism 14 onto outer surface 94 and inner surface 96 of the cutter mechanism 14. The abrasive sections 90A, 90B, 90C may be made abrasive by virtue of an abrasive composition (e.g., diamond) coated thereon. The cutter mechanism 14 further comprises a base 98, which in the illustrated examples of FIGS. 5A and 5B is not coated with an abrasive composition. Advantageously the alternating abrasive sections 90A, 90B, 90C and sharp sections 92A, 92B, 92C may produce the cleanest cut in all lesion morphologies and thus produce the least amount of particulate or smaller sized particles.

In the embodiment of FIG. 5A, the sharp sections 92A, 92B, 92C terminate at the annulus of the cutter mechanism 14 generally defined by the abrasive sections 90A, 90B, 90C such that the distal edges of the sharp sections 92A, 92B, 92C do not extend distally beyond the cutting edge 16. In the embodiment of FIG. 5B, the sharp sections 92A, 92B, 92C extend distally beyond the annulus of the cutter mechanism 14 generally defined by the abrasive sections 90A, 90B, 90C. Both embodiments of FIGS. 5A and 5B may comprise a slight taper on the inner surface 96 such that the inner diameter at the cutting edge 16 is larger than the inner diameter of a proximal annulus at the base 98.

The cutter mechanism 14 may be coupled to the distal section of the drive shaft 11 such that the cutter mechanism 14 rotates when the drive shaft 11 rotates. The cutter mechanism 14 thus is configured to cut occlusive material from a lesion within a blood vessel when the drive shaft 11 is rotated and at least one sharp section 92 and/or at least one abrasive section 90 is positioned in engagement with the occlusive material.

In some examples, the abrasive sections 90A, 90B, 90C have a flat or radius (i.e. not sharp) leading edge at cutting edge 16 that allows the abrasive coating to adhere to the cutter mechanism and not slough off during use. Sharp sections 92A, 92B, 92C are configured to make a clean cut in non-calcified lesion tissue while the abrasive sections 90A, 90B, 90C are configured to sand away hard (i.e. abrade) calcified components of a lesion. The abrasive coating on the outer and inner surfaces 94, 96 of the cutter mechanism 14 are raised above the sharp sections 92A, 92B, 92C, which may cause small impacts to the tissue at the distal edges of abrasive sections 90A, 90B, 90C, thereby providing shock waves that accelerate the breaking apart of hard calcified components of the lesion. The combination of the cutting ability of the sharp sections 92A, 92B, 92C with the sanding ability of the abrasive sections 90A, 90B, 90C and the micro impacts make for a cutting process that is more effective than just a sharp cutter or just an abrasive cutter in all types of lesion morphologies.

In still other examples, the outer and inner surfaces 94, 96 of the cutter mechanism 14 may be substantially entirely coated with the abrasive composition with the exception of the non-abrasive coated base 98 and the entirety of the cutting edge 16. In such examples, the entirety of the cutting edge 16 may provide a sharp section with cutting ability while sanding/abrading ability is provided by surfaces 94, 96.

In any such examples, the cutter mechanism (e.g., 14) may comprise at least two materials having different compositions and different hardnesses that comprise different surface hardnesses of the cutter mechanism. In any such examples the cutter mechanism generally may define a cup shape and the cutter mechanism generates the proximal flow of fluid and removed occlusive material by generating a pressure differential between the fluid within a fluid-filled tubular structure (e.g., blood vessel) and the lumen of the flexible elongate sheath (e.g., 34).

FIGS. 6-11 illustrate features of rotational device 50 that provide multi-stage maceration (e.g., of occlusive material). Advantageously, multi-stage maceration results in smaller and more consistently-sized particles of occlusive material traveling proximally through and out of the device 50, which may help reduce a likelihood of the device clogging. As generally described herein and as applicable to devices 10 and 50, multi-stage maceration is a 3 step process. First, as lesion tissue is cut, the tapered internal diameter of the cutter mechanism (e.g., cutter mechanism 14) forces the tissue into 3 multilevel shredding hooks that are part of the cutter mechanism, causing the tissue to tear or break into shorter lengths. The hooks may be curved and thus configured to act like a propeller forcing blood and lesion tissue to move into a second chopping stage of maceration that takes place at the macerator body (e.g., macerator body 30). The second stage has multiple cutting edges, half of which are stationary and the other half rotate. All cutting edges have sharp cutting angles. The higher pressure generated by the cutting hooks causes blood and tissue to flow proximal into a third maceration stage between the macerator body and the impeller (e.g., impeller 32) that also acts as a propeller as once again the tissue is chopped and further reduced in size, creating a slurry of blood with finely chopped lesion particles. In some examples, the device features that provide the multi-stage maceration may comprise different metallic materials (e.g., alloys) having different compositions and/or hardnesses.

FIG. 6 is a partial-cutaway drawing of the rotational device 50 of FIG. 2A with the proximal section 20 of the cutter shroud 18 and the cutting ring of the cutter mechanism 14 removed to illustrate three curved teeth (e.g., hooks) 100A, 100B, and 100C within the base 98 of the cutter mechanism 14, though more or fewer teeth or hooks may be provided in other examples. The teeth or hooks 100A, 100B, 100C chop tissue on a sharp edge 102 of the cutter guard when they rotate, as further illustrated in FIG. 7. The base 98 of the cutter mechanism 14 also has three sharp edges (not shown in FIG. 6) that chop tissue with the leading edges of the macerator body 30, as further illustrated in FIG. 8.

Figure 7:
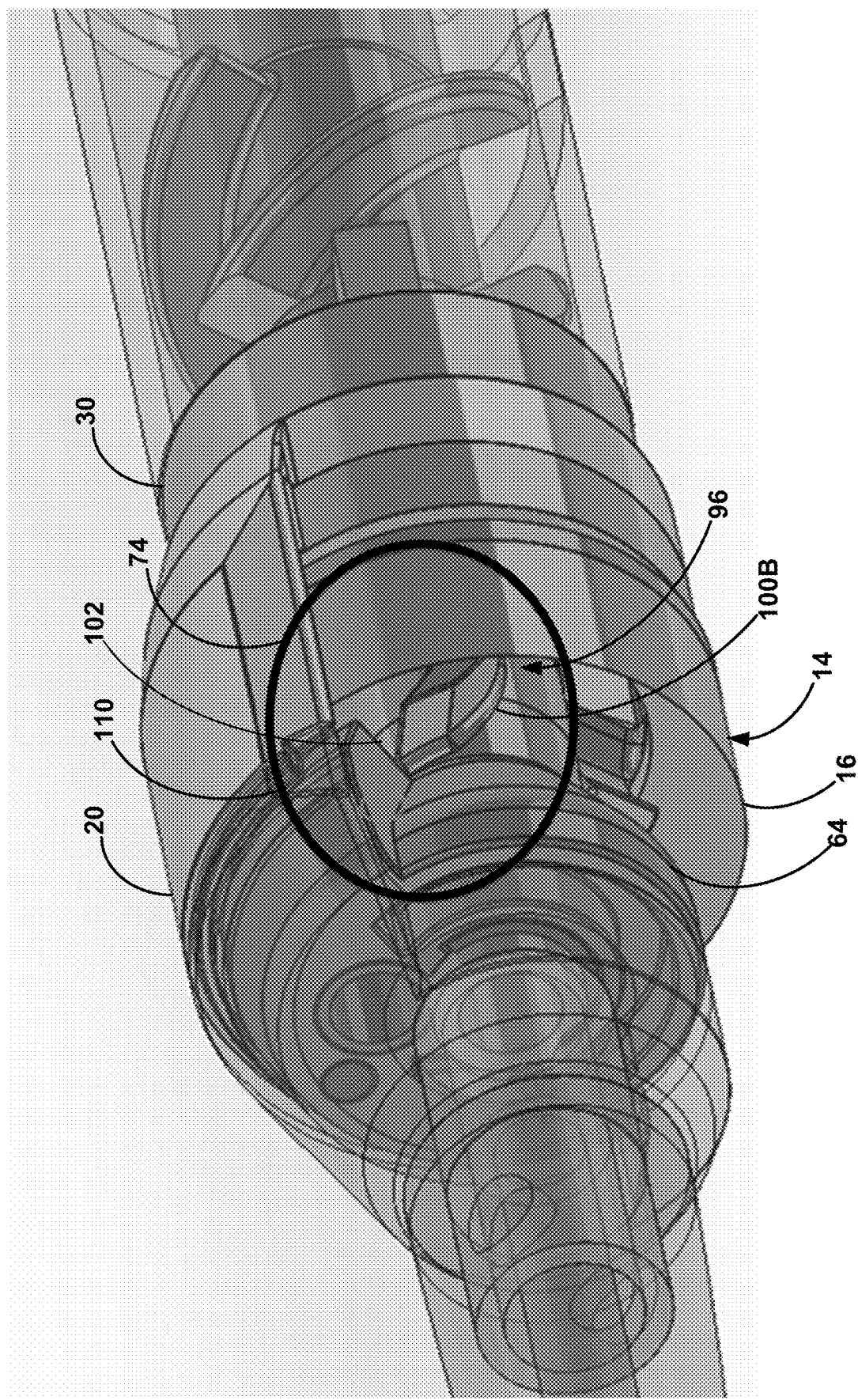
FIG. 7 is a perspective drawing of the rotational device of FIG. 2A illustrating a first stage of maceration between the movable cutter guard and the teeth of the base of the cutter mechanism.

FIG. 7 is a perspective drawing of the rotational device of FIG. 2A illustrating a first stage of maceration 110 occurring at an interface between the sharp edge 102 of the rotatably movable cutter guard 64 and the teeth or hooks 100A, 100B, 100C of the base 98 of the cutter mechanism 14. Once occlusive material has been cut from a lesion by the cutting edge 16, the tapered inner diameter of the inner surface 96 of the cutter mechanism 14 works to force the cut occlusive material between the sharp edge 102 of the cutter guard 64, which is in the open position, and the three shredding teeth or hooks 100A, 100B, 100C. The shredding teeth or hooks 100A, 100B, 100C are operatively connected with the drive shaft 11 and, therefore, rotate therewith to shred the cut occlusive material between the sharp edge 102 of the cutter guard and the teeth or hooks 100A, 100B, and 100C. The teeth or hooks 100A, 100B, 100C may be curved, as illustrated in FIG. 7, which may help force the shredded occlusive material proximally toward the second stage of maceration and generate proximal fluid flow. For example, a generated pressure differential and resultant fluid flow urges or drives the macerated occlusive material proximally from the first stage of maceration 110 to a second stage.

FIGS. 8A-8D are perspective, side, and front elevation drawings of the macerator body 30 of the rotational device 50 of FIG. 2A. Different features of the macerator body 30 provide maceration of occlusive material at the second and third maceration stages provided by the device 50 as further described below with respect to FIGS. 9 and 11.

As illustrated in FIGS. 8A-8D, the macerator body 30 may include a main body 130, a distal section 132 comprising a plurality (e.g., three) knife edges 134A, 134B, and 134C, a lumen 136 defined therethrough, which may be sized to receive the drive shaft 11, a proximal end 138, and a plurality (e.g., three) ribs 140A, 140B, and 140C extending from proximal end 138. The distal section 132 may have at least one outer diameter that is greater than an outer diameter of the main body 130 proximal to the distal section 132. Distal section 132 of the main body 130 generally may be sized and configured to interface with the base 98 of the cutter mechanism 14.

Figure 8B:
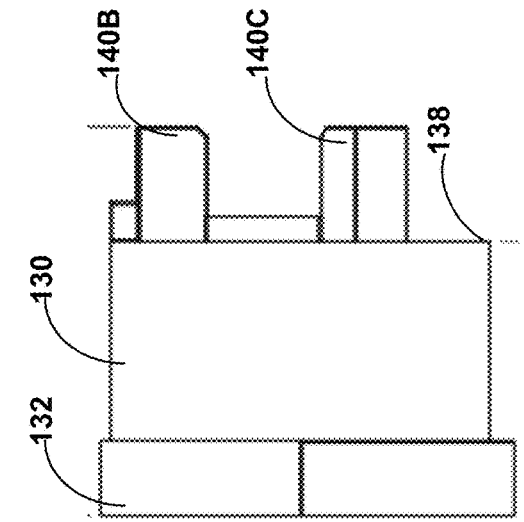
FIGS. 8A-8D are perspective, side, and front elevation drawings of a macerator body of the rotational device of FIG. 2A.
Figure 8D:
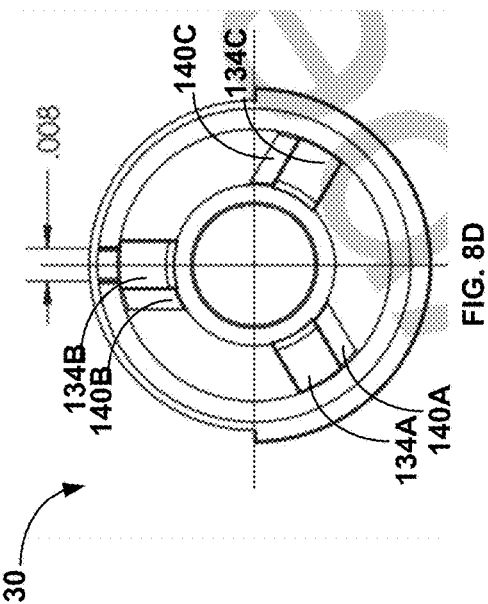
Figure 8A:
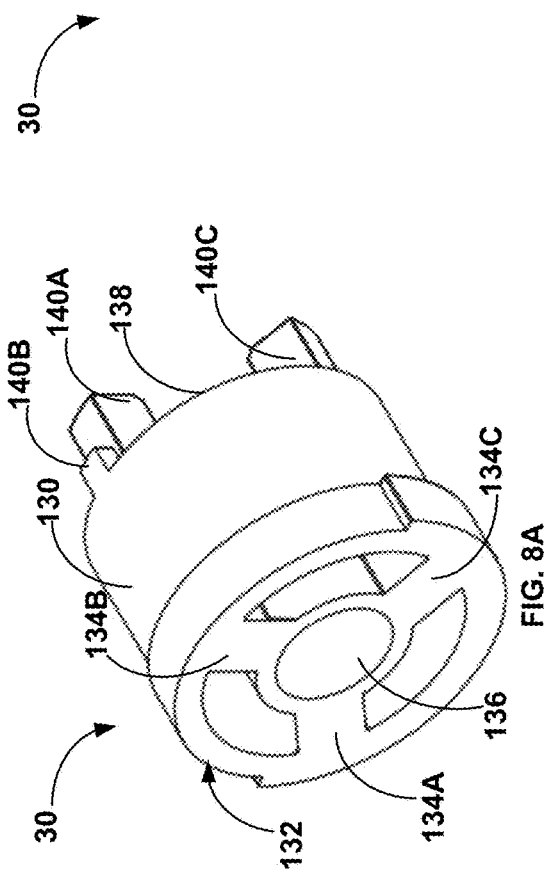
Figure 8C:
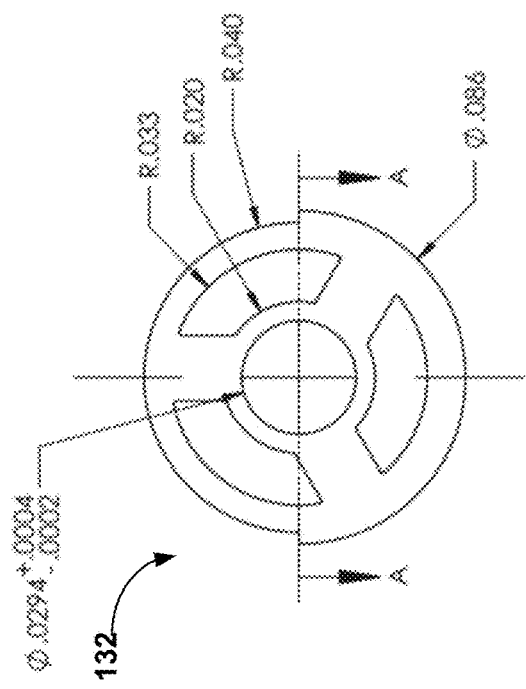

As shown in FIGS. 8A, 8B, and 8D, the knife edges 134A, 134B, and 134C at the distal section 132 of the macerator body 30 may be substantially aligned or slightly offset from the ribs 140A, 140B, and 140C extending from the proximal end 138 of the macerator body 30. In some examples, the distal section 132 of the macerator body 30, and thus the knife edges 134A, 134B, 134C, may be rotatable relative to the main body 130 while the ribs 140A, 140B, 140C are stationary relative to the main body 130. Features of the macerator body 30 may have any dimensions suitable for interacting with other components of the device 50, with several example dimensions indicated in FIGS. 8C and 8D (in inches).

Figure 9:
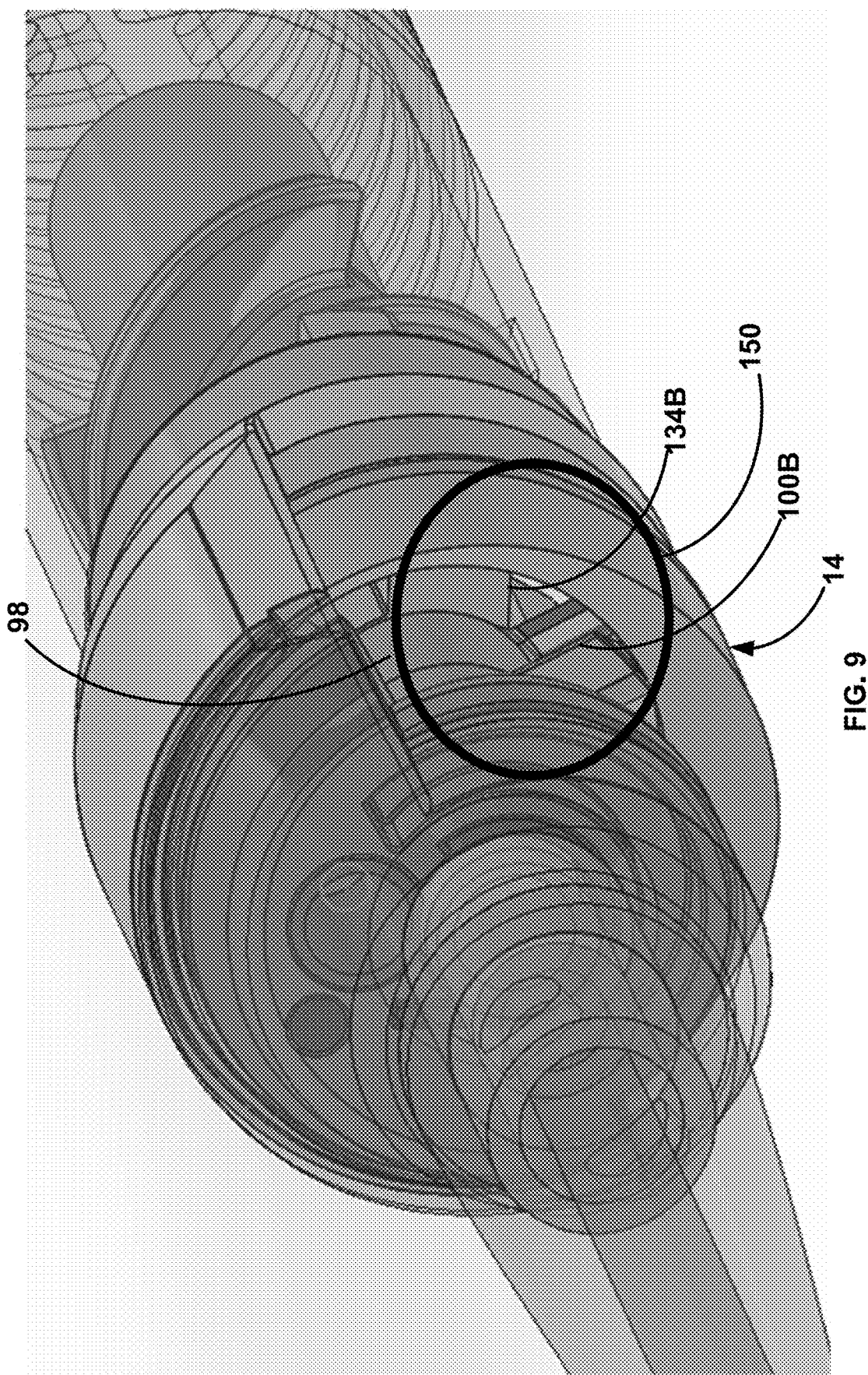
FIG. 9 is a longitudinal perspective drawing of the rotational device of FIG. 2A illustrating a second stage of maceration between the teeth of the base of the cutter mechanism and knife edges of the macerator body of the rotational device of FIG. 2A.
Figure 10:
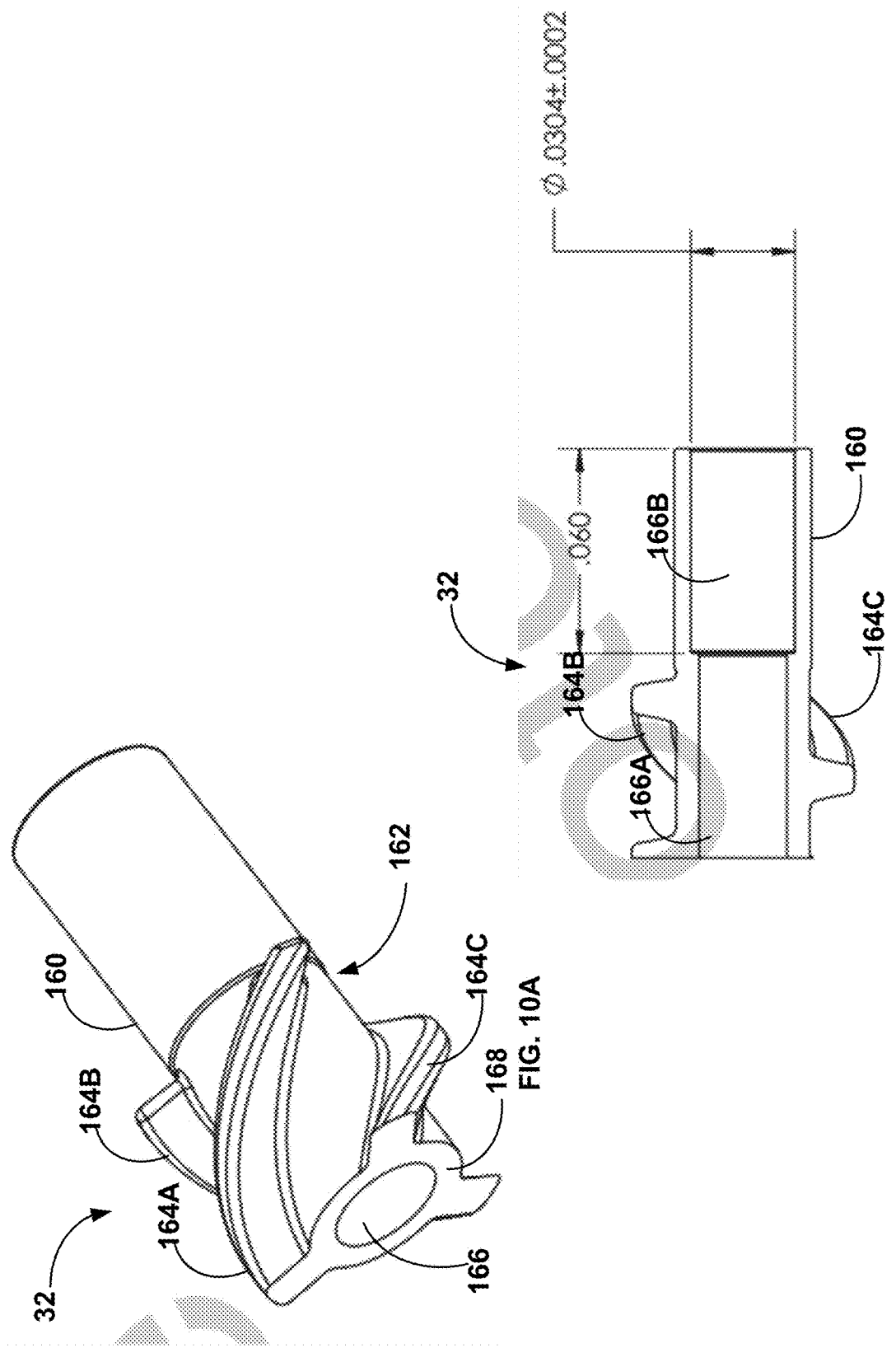
FIGS. 10A and 10B respectively are perspective and left-side drawings of an impeller of the rotational device of FIG. 2A.

FIG. 9 is a longitudinal perspective drawing of the rotational device of FIG. 2A illustrating a second stage of maceration 150 occurring between the teeth or hooks 100A, 100B, 100C of the base 98 of the cutter mechanism 14 and knife edges 134A, 134B, 134C of the distal section 132 of the macerator body 30 of the rotational device 50 of FIG. 2A. At the second stage of maceration 150, the macerator body receives the macerated material from the first stage 110, cuts the macerated material into smaller pieces of occlusive material between the teeth or hooks 100A, 100B, 100C of the base 98 of the cutter mechanism 14 and knife edges 134A, 134B, 134C of the distal section 132, and proximally force the smaller pieces of occlusive material toward the third stage of maceration when the drive shaft 11 is rotated. Similarly to the first stage of maceration, a generated pressure differential and resultant fluid flow urges or drives the macerated occlusive material proximally, this time from the second stage of maceration 150 to a third stage of maceration.

FIGS. 10A and 10B respectively are perspective and left-side drawings of an impeller of the rotational device of FIG. 2A. Features of the impeller 32 provide maceration of occlusive material at the third maceration stage provided by the device 50 as further described below with respect to FIG. 11. Impeller 32 includes a main impeller body 160, which further includes a distal section 162 that comprises a plurality (e.g., three) curved fins 164A, 164B, and 164C that define sharp leading edges. The main impeller body defines a lumen 166 therethrough, which may be sized to receive the drive shaft 11, and a distal end 168. As illustrated in FIG. 10B, the lumen 166 may define a distal section 166A having a first internal diameter that is smaller than a second internal diameter at a proximal section 166B of the lumen 166. In some such examples the first internal diameter is sized to receive the hypotube 42 of the drive shaft 11 and the second internal diameter is sized to receive a more-proximal portion of the drive shaft 11. Generally, features of the impeller may have any dimensions suitable for interacting with other components of the device 50, with several example dimensions indicated in FIG. 10B (in inches).

Figure 11:
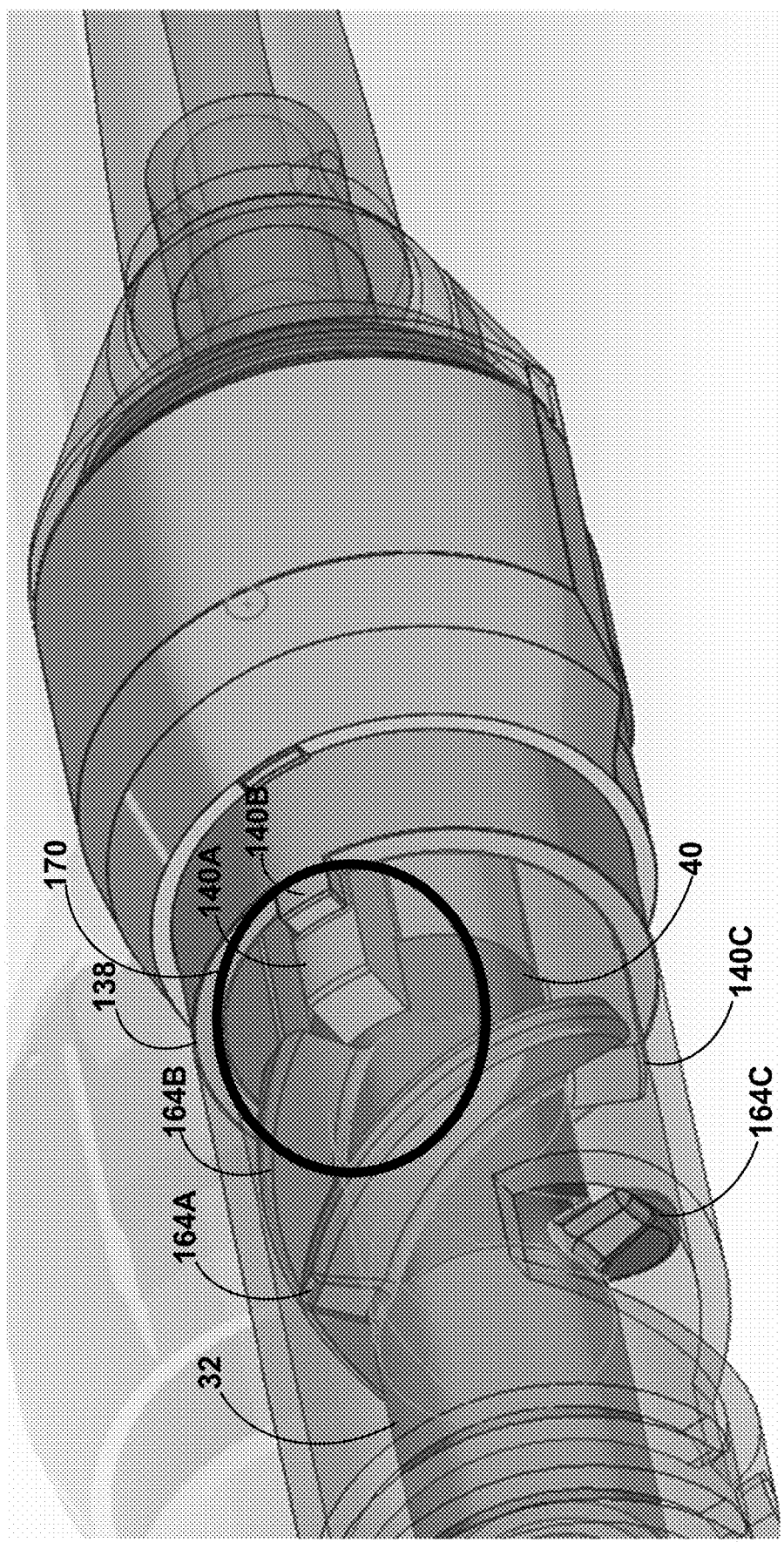
FIG. 11 is a longitudinal perspective drawing of the rotational device of FIG. 2A illustrating a third stage of maceration between ribs extending from a proximal end of the macerator body and sharp leading edges of an impeller of the rotational device of FIG. 2A.

FIG. 11 is a longitudinal perspective drawing of the rotational device of FIG. 2A illustrating a third stage of maceration 170 occurring between ribs 140A, 140B, 140C extending from proximal end 138 of the macerator body 30 and the sharp leading edges of the curved fins 164A, 164B, and 164C of the impeller 32 of the rotational device 50 of FIG. 2A. That is, at the third stage of maceration 170, the macerated material from the second stage 150 is cut into still-smaller pieces of occlusive material between the ribs 140A, 140B, 140C and the sharp leading edges of the curved fins 164A, 164B, and 164C when the drive shaft 11 is rotated. Similarly to the first and second stages of maceration, a generated pressure differential and resultant fluid flow urges or drives the macerated occlusive material proximally, this time from the third stage of maceration 170 into the lumen defined by the flexible elongate body (e.g., 34). The occlusive material, which has now been macerated into a fine slurry, is transported proximally for removal through the lumen of the flexible elongate sheath, aided by the helix-wound wire 56 of the drive shaft 11, as further illustrated in FIG. 12.

Figure 12:
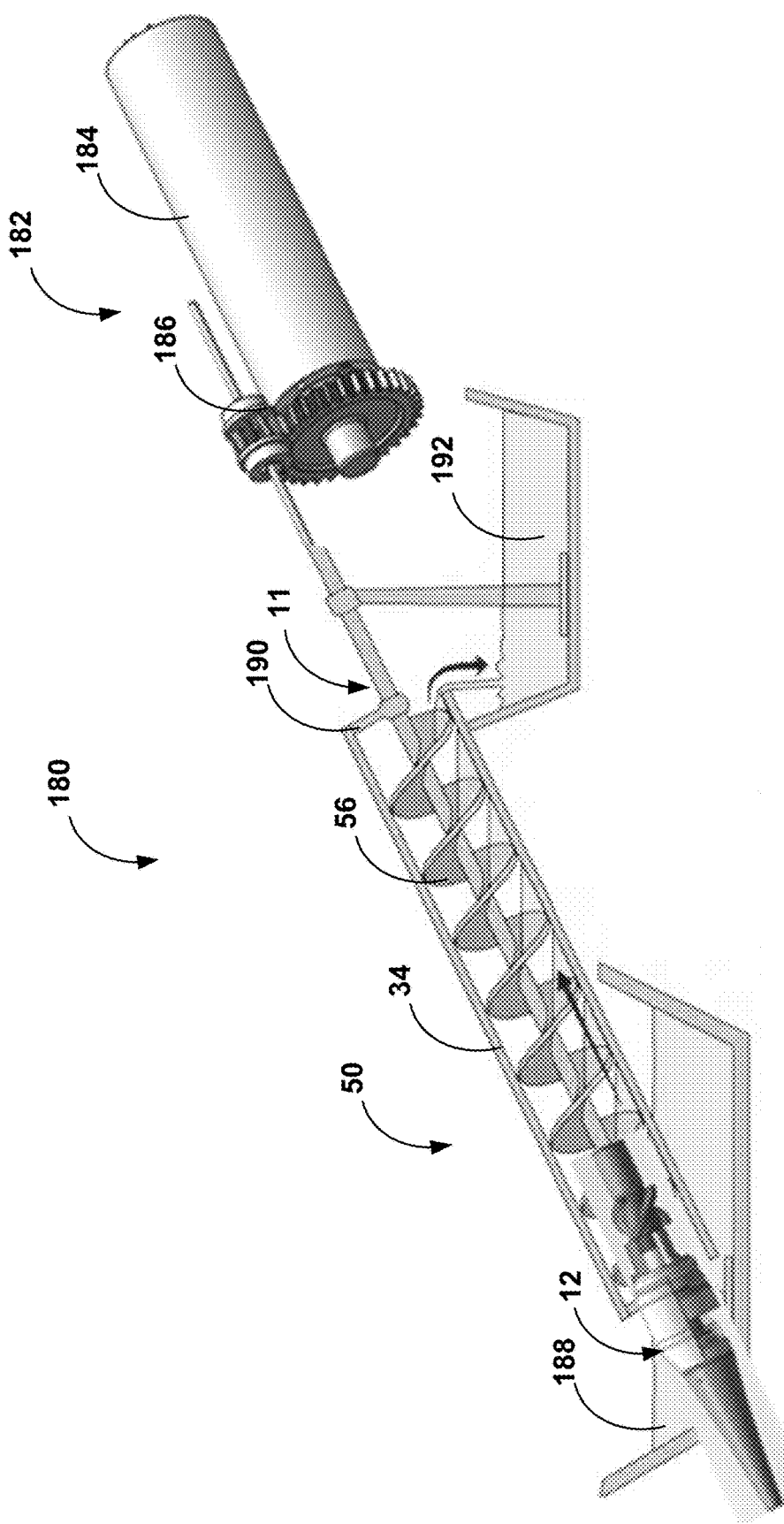
FIG. 12 is a perspective drawing of an atherectomy system including the rotational device of FIG. 2A.

FIG. 12 is a perspective drawing of an atherectomy system 180 including the rotational device 50 of FIG. 2A and a drive assembly 182 comprising a prime mover 184 (e.g. electrical motor or turbine) and a gear assembly 186 coupled to the drive shaft 11. As illustrated in FIG. 12, a fluid (e.g., a slurry of macerated occlusive material) may be pumped proximally through the device 50 by rotation of the drive shaft 11 and helix-wound wire 56 when the drive shaft 11 is rotated by the drive assembly 182. For example, the fluid may be moved proximally from a source 188 (e.g., the site of a lesion within a blood vessel), macerated and proximally moved through the distal tissue removal section 54 of the device 50, further proximally through a lumen defined by the flexible elongate sheath 34, and out a proximal end 190 of the flexible elongate sheath 34. In some examples, movement of the fluid proximally through the device 50 is entirely passive; i.e., provided solely by rotation of the drive shaft 11 and helix-wound wire 56 and a resulting pressure differential between the fluid within the blood vessel and the lumen of the flexible elongate sheath 34.

Additionally, or alternatively, aspiration and movement of material proximally through the device 50 may be vacuum-assisted. In such examples, the system 180 may include a powered pump, such as a distal-driven axial pump or a roller pump (not shown in FIG. 12) external to the flexible elongate sheath 34 to create negative pressure. The powered pump in such examples may create at a minimum of two different vacuum pressures. The additional negative pressure provided by the powered pump assists in pulling the liquid slurry within and through the device 50. This combination of mechanical pumping and vacuum assist allows the device 50 to treat unlimited lesion lengths and passes without stopping to remove occlusive material.

In any such examples, at the point that the fluid exits the proximal end 190 of the flexible elongate sheath 34, it is outside of the patient's body. For the sake of illustration, fluid is shown in FIG. 12 as directly exiting the proximal end 190 of the flexible elongate sheath 34 into a container 192. However, in actual use, the fluid then may be transported to a collection bag via a waste line (not shown) upon exiting the proximal end 190 of the flexible elongate sheath. This is further illustrated and described below with respect to FIG. 14.

Figure 13A:
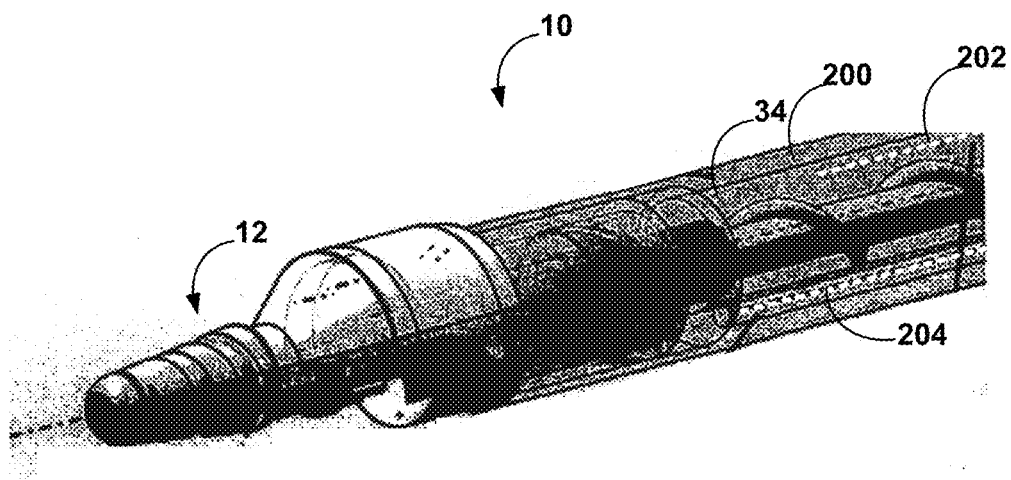
FIGS. 13A-13C are perspective and left-side drawings of the device of FIG. 1A illustrating the steerability of an elongate sheath and distal cutting section of the device of FIG. 1A.
Figure 13B:
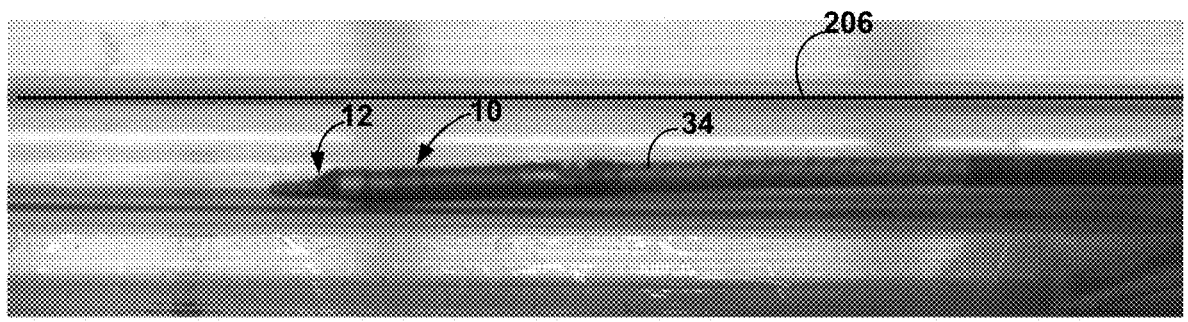
Figure 13C:
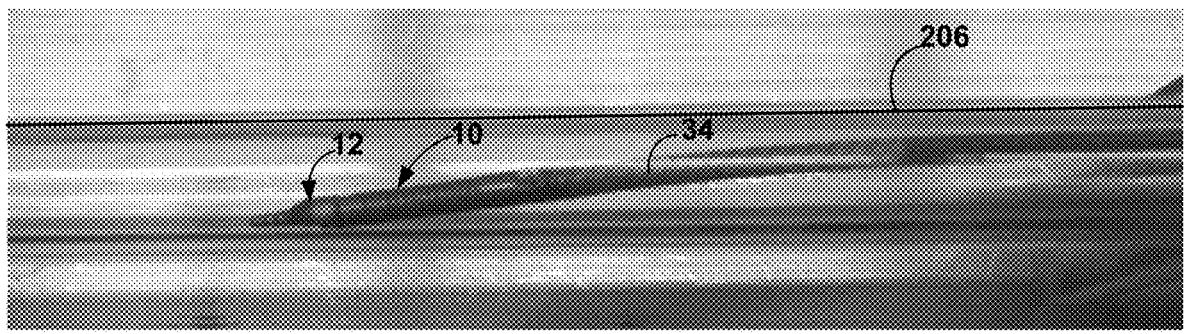

FIGS. 13A-13C are perspective and left-side drawings of the device 10 of FIG. 1A illustrating the steerability of the flexible elongate sheath 34 and the distal tissue removal section 12 of the device 10. It should be noted that the following description of the steerability of the flexible elongate sheath is equally applicable to the device 50 and distal tissue removal section 54 of FIG. 2A. In some examples, the steerability of the device 10 may be provided by at least one pull wire, which may be embedded in a wall 200 of the flexible elongate sheath 34 or otherwise positioned therein. For example, as shown in FIG. 13A, the device 10 may include a proximal pull wire 202 and/or a distal pull wire 204, one or both of which may be substantially similar to the pull wire 63 of the device 50 illustrated in FIG. 2A. In such examples the pull wire(s) 202 and/or 204 enable steerability of the flexible elongate sheath 34 and the distal tissue removal section 12 in multiple planes of movement to provide precise positioning of the cutter mechanism 14. In some examples, the flexible elongate sheath 34 also may be rotatable up to 360 degrees to aid steering and positioning of the device 50.

This steerability provided by the wire(s) 202 and/or 204 provides superior positioning ability to the distal tissue removal section 12 by enabling movement of the distal tissue removal section 12 in both a first direction and a second and opposite direction within a single plane. This feature helps keep the cut angle of the cutter mechanism 14 more consistent over a wider range of vessel inside diameters as well as enabling the de-bulking lesions within a curve. This ability to keep the cutter mechanism 14 substantially parallel relative to the lumen defined by the blood vessel is an important safety feature that reduces the chance of undesirable dissection. Also notable is that the steerability provided by the wire(s) 202 and/or 204 allows the distal tissue removal section 12 to move beyond the path of just following a guide wire, thus allowing for a wider or more specific cutting path than devices that just follow a guide wire. The pull wire(s) 202 and/or 204 may be actuated by a handle coupled to a distal end of said wire(s) as further discussed below with respect to FIGS. 14 and 15.

FIGS. 13B and 13C illustrate an example of the steerability of the distal tissue removal section 54 and flexible elongate sheath 34 provided by the wire(s) 202 and/or 204. As shown in FIG. 13B, the device 10 has been advanced within a vessel 206. In FIG. 13C, the pull wire(s) 202 and/or 204 have been actuated (e.g., pulled proximally), causing the flexible elongate sheath 34 assume a Z- or an S-shape and to back up onto a wall of the vessel 206 opposite a treatment site, forcing the cutter mechanism 14 of the distal tissue removal section 12 into a lesion (not shown). The wall of the vessel 206 opposite the treatment site thus is a contact point for the flexible elongate sheath 34 that provides deflection force for the sheath 34.

Figure 14:
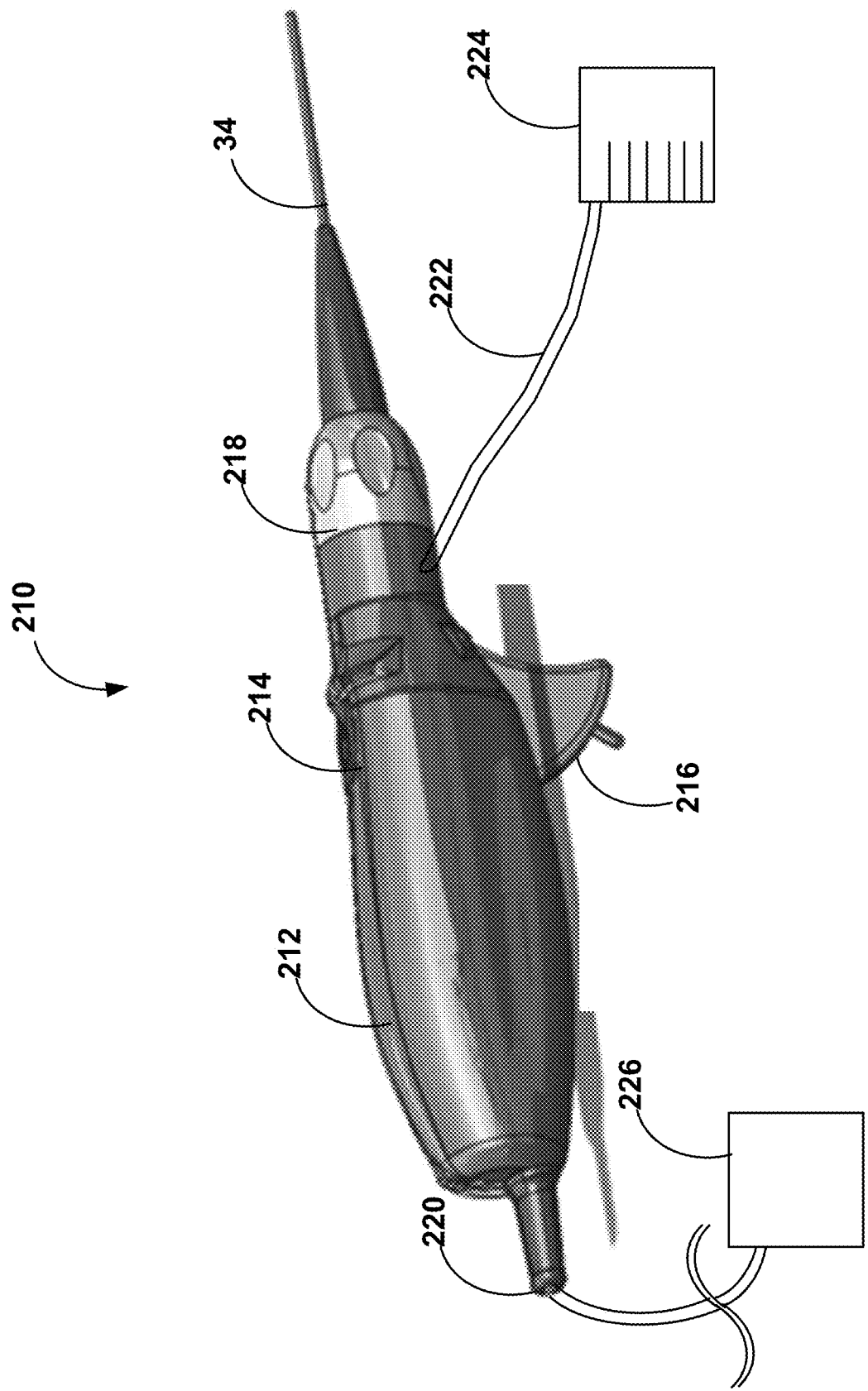
FIG. 14 is a perspective drawing of a handle assembly of an atherectomy system including the device of FIG. 2A in accordance with this disclosure.

FIG. 14 is a perspective drawing of a handle assembly 210 of an atherectomy system (e.g., the system 180 of FIG. 12) that includes the device 50 of FIG. 2A. Handle assembly 210 may include a main body 212, a cutter spin on/off button 214 enabling selective activation of rotation of the drive shaft 11, a tip deflection trigger mechanism 216, which when actuated may provide about a 3-9 mm offset of the distal tissue removal section 54, a rotating tip 218 configured to rotate to an index cutter position, and an effluent line 220/back-loadable guide wire area at a proximal end of the handle assembly 210. The handle assembly 210 desirably contains a direct current (DC) motor, a turbine, or other suitable prime mover for rotating the drive shaft 11 at high speeds.

The handle assembly 210 may be connected to any suitable power source. In examples in which the handle assembly 210 comprises a DC motor, the power source may supply electric current to the handle assembly 210 to power rotation of the drive shaft 11. In examples in which the handle assembly 210 comprises a turbine, the power source may be a source of pneumatic energy; e.g., compressed air delivered via a tube to the handle assembly 210. In any such examples the system further may include a controller (not shown) configured to manage power supply to the handle assembly 210 and drive shaft 11 and/or means for obtaining current and torque feedback from the device 50 to enable determination of location and cutting capability. In some examples, means for monitoring the speed of rotation of the turbine and drive shaft 11, such as one or more fiber optic cables (not shown) may be provided. Details regarding such handles and associated instrumentation are well known in the industry, and are described, e.g., in U.S. Pat. No. 5,314,407, issued to Auth. In some examples a re-usable power brick (not shown) may be used with the system and may include features such as an LED for system error indication. The power source may be connected to a computing device (not shown) comprising software configured to provide control of one or more aspects of system operation.

The drive shaft 11 and flexible elongate sheath 34 may be coupled to the rotating tip 218. A waste line 222 and fluid-collection bag 224 optionally may be coupled to the handle assembly 210 proximally of the rotating tip 218, as shown in FIG. 14. The collection bag 224 may be clear with graduated markings to enable a user to track the total volume of fluid removed during a procedure and help ensure patient safety.

Optionally, a powered pump 226 may be coupled to the handle assembly 210 at the effluent line 220/back-loadable guide wire area at the proximal end of the handle assembly 210. Powered pump 226 may be a distal-driven axial pump or a roller pump configured to create negative pressure through flexible elongate sheath 34; e.g., at a minimum of two different vacuum pressures. The additional negative pressure provided by powered pump 226 assists in pulling the liquid slurry within and through the device 50 and into the collection bag 224. In examples in which the powered pump 226 is included a make-up fluid line (not shown) may be connected to a standard saline bag and protect against air ingress should the tip clog during use.

Figure 15:
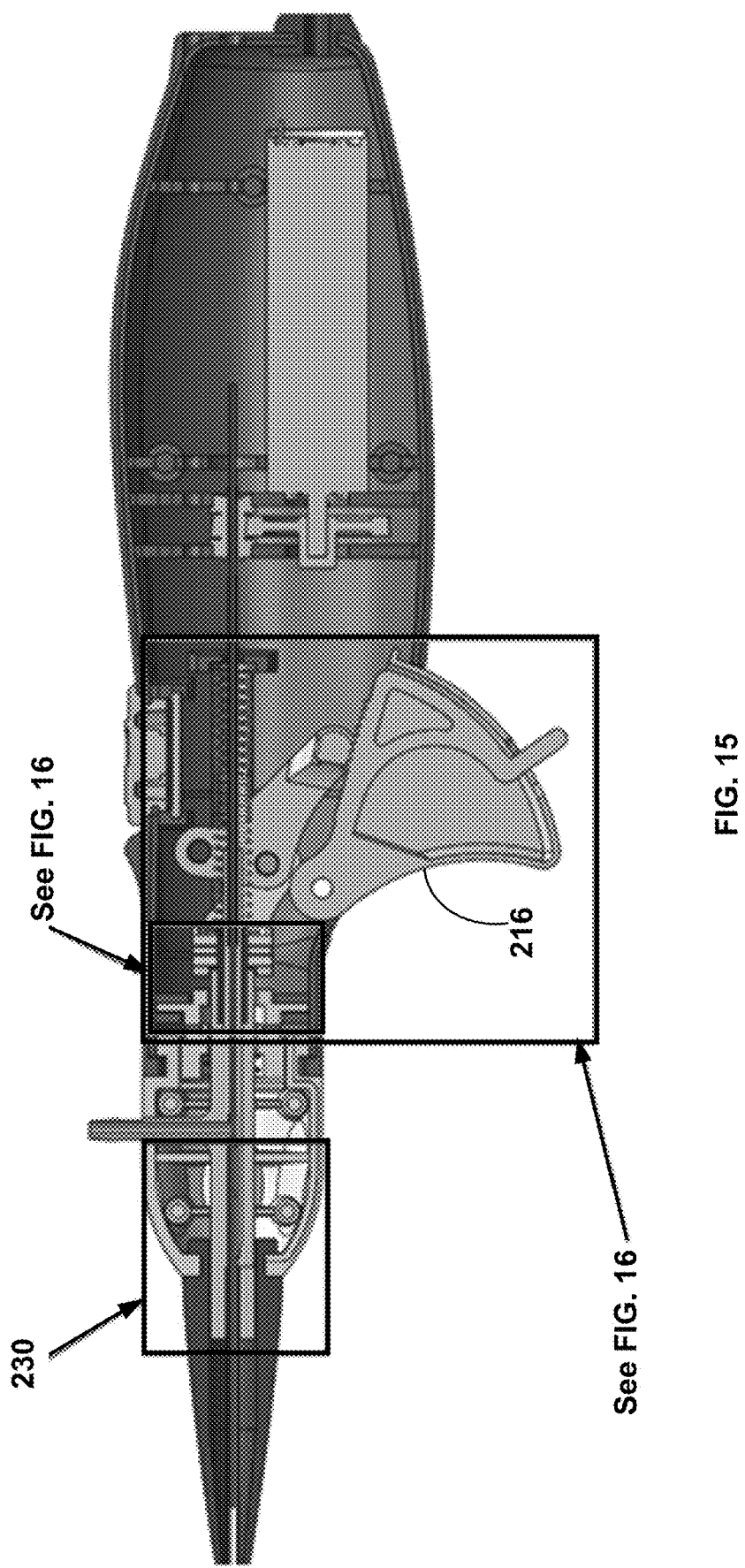
FIG. 15 is a longitudinal cross-section of the handle assembly of FIG. 14.

FIG. 15 is a longitudinal cross-section of the handle assembly 210 of FIG. 14. FIG. 15 illustrates a sheath bond and pull-wire exit region 230 near a distal end of the handle assembly 210. FIG. 15 also provides an overview of portions of handle assembly 210 that are presented in greater detail in FIGS. 16 and 17, including the tip deflection trigger mechanism 216 and a point of attachment of pull wire 202 to trigger mechanism 216.

Figure 16:
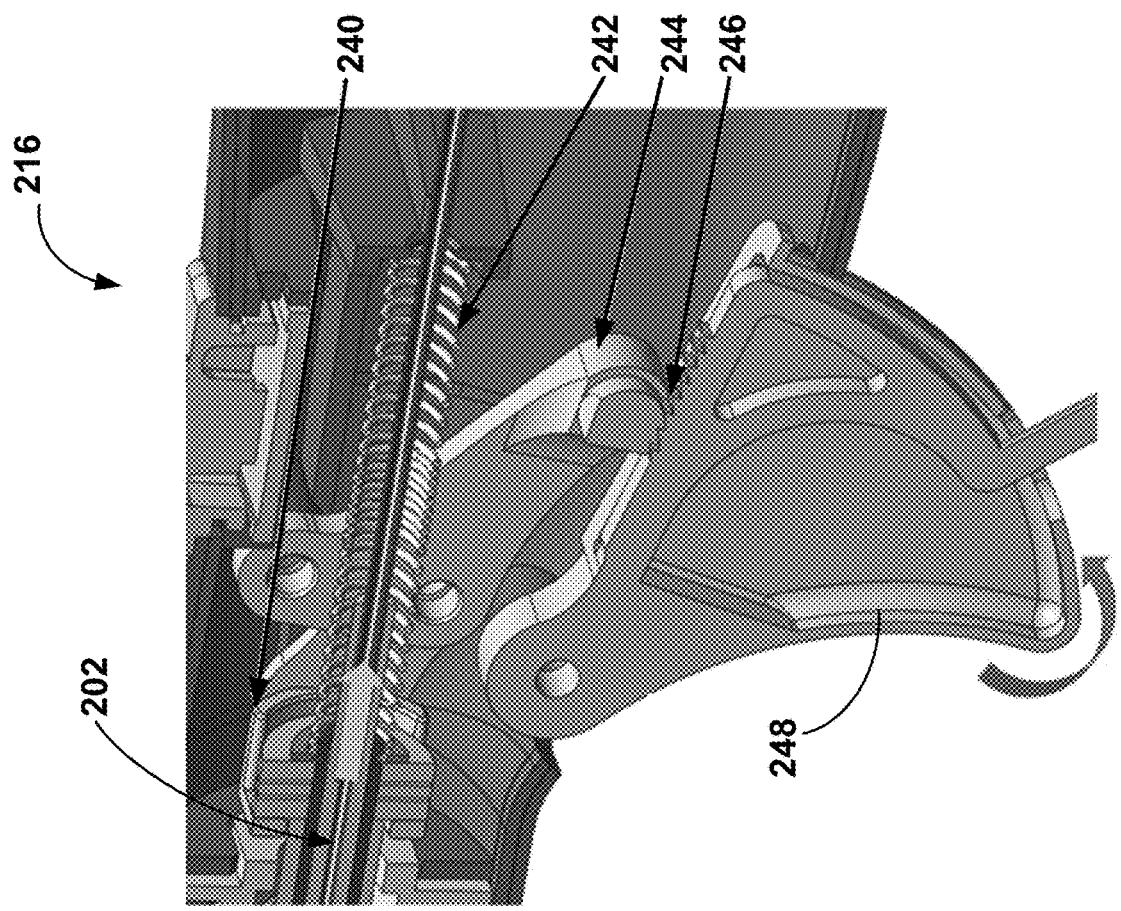
FIG. 16 is a longitudinal cross-section illustrating a portion of the cross-section of FIG. 15 in further detail.

FIG. 16 is a longitudinal cross-section illustrating a portion of the cross-section of FIG. 15 in further detail. Specifically, FIG. 16 illustrates further components of the tip deflection trigger mechanism 216 of the handle assembly 210, which enables actuation of the pull wire(s) 202 and/or 204. For the sake of clarity only pull wire 202 is illustrated in FIG. 16. As illustrated in FIG. 16, components of the tip deflection trigger mechanism includes a bearing cup 240, a return spring 242, a trigger linkage 244, and a trigger lock/release 246. Actuation of the trigger mechanism 216 moves the proximal pull wire 202 in a proximal direction (direction of arrow), which deflects the flexible elongate sheath 34 and the distal cutting section 12 as discussed above.

Figure 17:
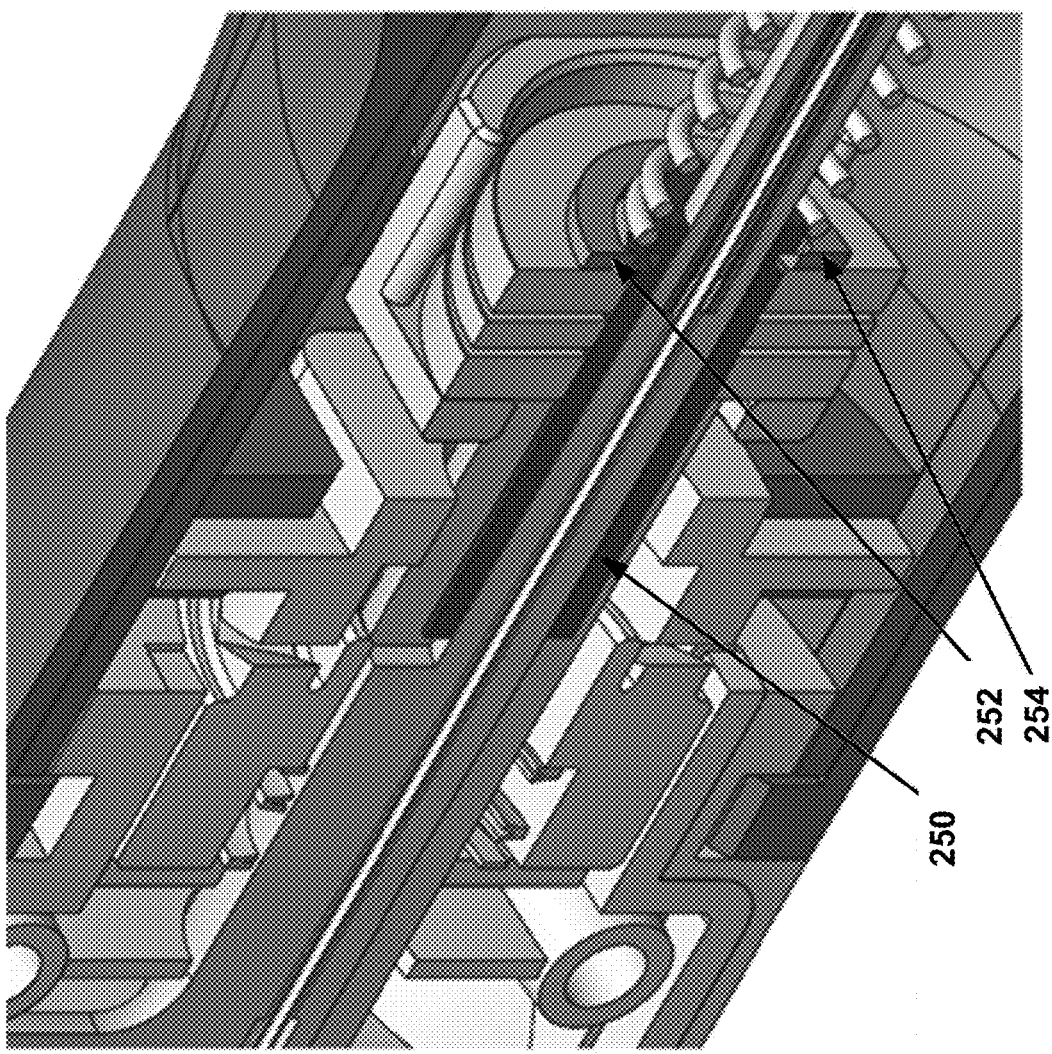
FIG. 17 is a longitudinal cross-section illustrating another portion of the cross-section of FIG. 15 in further detail.

FIG. 17 is a longitudinal cross-section illustrating a portion of the cross-section of FIG. 15 in further detail. Specifically, FIG. 17 illustrates a point of attachment of pull wire 202 to trigger mechanism 216. As illustrated in FIG. 17, the point of attachment of pull wire 202 to trigger mechanism 216 includes a pull wire collar 250, a pull wire retaining clip 252, and a thrust bearing 254. This design enables the user of device 50 to easily index the rotating tip 218 to the index cutter position and to easily deflect the flexible elongate sheath 34 and distal cutting section 56. The thrust bearing 254 also enables rotation of the flexible elongate sheath 34 during deflection. The aspiration lumen defined by the flexible elongate sheath 34 includes a rotary seal that enables aspiration within the flexible elongate sheath 34 when the flexible elongate sheath 34 is rotated to any position, while the aspiration lumen exit remains fixed within and exiting the handle assembly 210.

The following section sets forth several embodiments of the devices, systems, and methods described herein. The following embodiments are divided into four categories according to subject matter for the sake of clarity but should be understood as being non-limiting in nature. Each category contains a numeric listing of embodiments beginning with an embodiment no. 1. Features of the embodiments from any of the four categories below may be combined and/or substituted with one another in any suitable manner.

Embodiments Comprising a Cutter-Mechanism Guard

1. A rotational device for removing occlusive material within a fluid-filled tubular structure, comprising: a drive shaft configured for insertion into the fluid-filled tubular structure, the drive shaft defining a distal section; a cutter mechanism disposed on the distal section of the drive shaft such that the cutter mechanism rotates when the drive shaft rotates, the cutter mechanism comprising a cutting edge configured to remove occlusive material from a lesion within the fluid-filled tubular structure when the drive shaft is rotated and the cutter mechanism is positioned in engagement with the occlusive material; and a cutter mechanism guard disposed on the distal section of the drive shaft, the cutter mechanism guard extending radially outwardly from the cutter mechanism and rotatable between: a first position wherein the cutter mechanism guard surrounds at least a portion of the cutting edge and prevents the cutting edge from engaging the occlusive material; and a second position wherein the cutter mechanism exposes the portion of the cutting edge to enable the cutting edge to engage and remove the occlusive material, wherein rotation of the drive shaft generates friction and vortex flow within the fluid in the fluid-filled tubular structure, and wherein the friction and the vortex flow cause the cutter mechanism guard to rotate between the first position and the second position.

2. The rotational device of embodiment 1, wherein the rotation of the drive shaft comprises rotation in a first rotational direction, and wherein rotation of the drive shaft in a second rotational direction generates friction and vortex flow within the fluid in the fluid-filled tubular structure that cause the cutter mechanism guard to rotate between the second position and the first position.

3. The rotational device of embodiment 1, wherein rotation of the cutter mechanism guard between the first position and the second position comprises a rotation of approximately 180 degrees about a longitudinal axis defined by the drive shaft.

4. The rotational device of embodiment 1, further comprising an elongate flexible sheath disposed radially outwardly of the drive shaft and defining a distal section positioned proximal to the cutter mechanism.

5. The rotational device of embodiment 4, wherein the cutter mechanism generates a proximal flow of fluid and removed occlusive material from the cutter mechanism to an inner diameter of the sheath when the cutter mechanism is rotated within the fluid-filled tubular structure.

6. The rotational device of embodiment 5, wherein the cutter mechanism further comprises a cutting ring base proximal to the cutting edge, the cutting ring base comprising a plurality of staggered cutting teeth positioned within an inner diameter of the cutting ring base, and wherein the staggered cutting teeth are configured to macerate occlusive material removed from the lesion by the cutting edge when the drive shaft is rotated.

7. The rotational device of embodiment 6, wherein the cutter mechanism guard defines a sharp edge, and wherein the sharp edge of the cutter mechanism guard is configured to assist the cutting teeth in macerating the occlusive material removed from the lesion by the cutting edge.

8. The rotational device of embodiment 1, further comprising a cutter shroud disposed on the distal section of the drive shaft radially outwardly from a portion of the cutter mechanism that is not surrounded by the cutter mechanism guard when the cutter mechanism guard is in the first position.

9. The rotational device of embodiment 4, further comprising a helix-wound wire extending around at least a portion of an outer diameter of the drive shaft, wherein the helix-wound wire forces fluid and removed occlusive material proximally through an inner diameter of the sheath when the cutter mechanism is rotated within the fluid-filled tubular structure.

10. The rotational device of embodiment 4, further comprising a pull wire, the pull wire defining a proximal portion extending proximally of the sheath and a distal portion extending longitudinally within a wall of the sheath to the distal section of the sheath.

11. The rotational device of embodiment 10, wherein a proximal pulling force applied to the proximal portion of the pull wire causes the distal section of the sheath to deflect.

12. The rotational device of embodiment 11, wherein the deflection of the distal section of the sheath moves the distal section of the sheath into contact with an inner surface of the fluid-filled tubular structure opposite the lesion such that the cutting edge is forced into the occlusive material.

13. The rotational device of embodiment 1, further comprising a flexible distal tip coupled to the distal section of the drive shaft.

14. A system comprising the rotational device of embodiment 5, the system further comprising a roller pump coupled to the device and configured to create a plurality of vacuum pressures to draw fluid and removed occlusive material proximally through a lumen defined by the sheath.

15. The system of embodiment 14, further comprising a collection bag coupled to the device via a fluid line, the collection bag configured to receive the fluid and removed occlusive material drawn proximally through the lumen of the sheath, the collection bag comprising a plurality of graduated volumetric markings.

16. The system of embodiment 15, further comprising means for obtaining current and torque feedback from the device to enable determination of location and cutting capability.

17. The system of embodiment 14, further comprising a handle coupled to the device, the handle comprising a prime mover configured to drive rotation of the drive shaft.

18. The system of embodiment 17, wherein the handle further comprises a trigger coupled to the pull wire to control deflection of the distal section of the sheath.

19. The system of embodiment 17, further comprising a guide wire, wherein the handle further comprises a guide wire management system comprising one of an external guide wire brake and a pre-loaded torquer.

Embodiments Comprising a Cutting-Depth Control Feature

1. A rotational device for removing occlusive material within a fluid-filled tubular structure, comprising: a drive shaft configured for insertion into the fluid-filled tubular structure, the drive shaft defining a distal section; a cutter mechanism disposed on the distal section of the drive shaft such that the cutter mechanism rotates when the drive shaft rotates, the cutter mechanism comprising a cutting edge configured to remove occlusive material from a lesion within the fluid-filled tubular structure when the drive shaft is rotated and the cutter mechanism is positioned in engagement with the occlusive material; a cutter shroud coupled to the distal section of the drive shaft, the cutter shroud defining a proximal section surrounding a portion of the cutter mechanism and defining a distal section extending distally of the cutting edge, wherein the distal section of the cutter shroud defines a tapered profile such that a first outer diameter at a proximal end of the distal section of the cutter shroud is greater than a second outer diameter of the distal section of the cutter shroud at a distal end of the distal section of the cutter mechanism, and wherein the distal section of the cutter shroud is configured to limit the depth to which the cutting edge penetrates the lesion during removal of the occlusive material from the lesion; and a cutting-depth control member comprising a distal section of the cutter shroud and an inner cutting-depth control member, wherein the inner cutting-depth control member defines a tapered profile such that a first outer diameter of the inner cutting-depth control member at the cutting edge is less than a second outer diameter of the inner cutting-depth control member distal to the cutting edge, and wherein the tapered profile of the inner cutting-depth control member is configured to control cutting depth and draw occlusive material proximally toward the cutting edge as the inner cutting-depth control member is advanced along the lesion.

2. The rotational device of embodiment 1, wherein the distal section of the cutter shroud limits the depth to which the cutting edge penetrates the lesion to a difference between the first diameter of the distal section of the cutter shroud and a diameter of the cutter mechanism at the cutting edge.

3. The rotational device of embodiment 1, further comprising a rotatable cutter mechanism guard comprising the inner depth-control member, the cutter mechanism guard further comprising an outer portion extending partially around an outer diameter of the cutter mechanism, wherein the cutter mechanism guard is rotatable between: a first position wherein the cutter mechanism guard surrounds at least a portion of the cutting edge and prevents the cutting edge from engaging the occlusive material; and a second position wherein the cutter mechanism guard exposes the portion of the cutting edge to enable the cutting edge to engage and remove the occlusive material.

4. The rotational device of embodiment 1, further comprising an elongate flexible sheath defining a lumen and a distal section positioned proximal to the cutter mechanism, the drive shaft at least partially received within the lumen.

5. The rotational device of embodiment 4, wherein the cutter mechanism generates a proximal flow of fluid and removed occlusive material from the cutter mechanism to an inner diameter of the sheath when the cutter mechanism is rotated within the fluid-filled tubular structure.

6. The rotational device of embodiment 5, wherein the cutter mechanism further comprises a cutting ring base proximal to the cutting edge, the cutting ring base comprising a plurality of staggered cutting teeth positioned within an inner diameter of the cutting ring base, and wherein the staggered cutting teeth are configured to macerate occlusive material removed from the lesion by the cutting edge when the drive shaft is rotated.

7. The rotational device of embodiment 4, further comprising a helix-wound wire extending around at least a portion of an outer diameter of the drive shaft, wherein the helix-wound wire forces fluid and removed occlusive material proximally through an inner diameter of the sheath when the cutter mechanism is rotated within the fluid-filled tubular structure.

8. The rotational device of embodiment 4, further comprising a pull wire, the pull wire defining a proximal portion extending proximally of the sheath and a distal portion extending longitudinally within a wall of the sheath to the distal section of the sheath.

9. The rotational device of embodiment 8, wherein a proximal pulling force applied to the proximal portion of the pull wire causes the distal section of the sheath to deflect.

10. The rotational device of embodiment 9, wherein the deflection of the distal section of the sheath moves the distal section of the sheath into contact with an inner surface of the fluid-filled tubular structure opposite the lesion such that the cutting edge is forced into the occlusive material.

11. The rotational device of embodiment 1, further comprising a flexible distal tip coupled to the distal section of the drive shaft.

12. A system comprising the rotational device of embodiment 4, the system further comprising a roller pump coupled to the device and configured to create a plurality of vacuum pressures to draw fluid and removed occlusive material proximally through a lumen defined by the sheath.

13. The system of embodiment 12, further comprising a collection bag coupled to the device via a fluid line, the collection bag configured to receive the fluid and removed occlusive material drawn proximally through the lumen of the sheath, the collection bag comprising a plurality of graduated volumetric markings.

14. The system of embodiment 13, further comprising means for obtaining current and torque feedback from the device to enable determination of location and cutting capability.

15. The system of embodiment 14, further comprising a handle coupled to the device, the handle comprising a prime mover configured to drive rotation of the drive shaft.

16. The system of embodiment 15, wherein the handle further comprises a trigger coupled to the pull wire to control deflection of the distal section of the sheath.

17. The system of embodiment 15, further comprising a guide wire, wherein the handle further comprises a guide wire management system comprising one of an external guide wire brake and a pre-loaded torquer.

Embodiments Comprising a Dual Interrupted Cutting and Sanding Cutter Mechanism

1. A rotational device for removing occlusive material within a fluid-filled tubular structure, comprising: a drive shaft configured for insertion into the fluid-filled tubular structure, the drive shaft defining a distal section; a cutter mechanism coupled to the distal section of the drive shaft such that the cutter mechanism rotates when the drive shaft rotates, the cutter mechanism comprising: a distal cutting edge configured to cut occlusive material from a lesion within the fluid-filled tubular structure when the drive shaft is rotated and the distal cutting edge is positioned in engagement with the occlusive material, wherein the distal cutting edge comprises at least one abrasive section coated with an abrasive composition and at least one sharp section that is not coated with the abrasive composition; and a major outer surface coated with the abrasive composition and configured to abrade calcified occlusive material from within the fluid-filled tubular structure when the drive shaft is rotated and the abrasive surface of the cutter mechanism is positioned in engagement with the calcified occlusive material.

2. The rotational device of embodiment 1, wherein the distal cutting edge comprises a flat leading edge configured to enable the abrasive composition to adhere to the at least one abrasive section of the distal cutting edge.

3. The rotational device of embodiment 2, wherein the major outer surface comprises at least one section that is not coated with the abrasive composition.

4. The rotational device of embodiment 2, wherein the at least one abrasive section of the distal cutting edge extends distally of the at least one sharp section of the distal cutting edge, wherein the abrasive composition of the major outer surface is raised above the at least one section of the major outer surface that is not coated with the abrasive composition.

5. The rotational device of embodiment 1, wherein the abrasive composition comprises a diamond coating.

6. The rotational device of embodiment 1, further comprising an elongate flexible sheath disposed radially outwardly of the drive shaft and defining a distal section positioned proximal to the cutter mechanism.

7. The rotational device of embodiment 6, wherein the cutter mechanism generates a proximal flow of fluid and removed occlusive material from the cutter mechanism to an inner lumen defined by the sheath when the cutter mechanism is rotated within the fluid-filled tubular structure.

8. The rotational device of embodiment 7, wherein the cutter mechanism defines a cup shape and the cutter mechanism generates the proximal flow of fluid and removed occlusive material by generating a pressure differential between the fluid within the fluid-filled tubular structure and the lumen of the sheath.

9. The rotational device of embodiment 6, wherein the cutter mechanism further comprises a cutting ring base proximal to the cutting edge, the cutting ring base comprising a plurality of staggered cutting hooks positioned within an inner diameter of the cutting ring base, and wherein the staggered cutting hooks are configured to macerate occlusive material removed from the lesion by the cutting edge when the drive shaft is rotated.

10. The rotational device of embodiment 9, further comprising a cutter mechanism guard coupled to the distal section of the drive shaft radially outwardly from the cutter mechanism, the cutter mechanism guard defining a sharp edge, and wherein the sharp edge of the cutter mechanism guard is configured to assist the cutting hooks in macerating the occlusive material removed from the lesion by the cutting edge.

11. The rotational device of embodiment 10, wherein the cutter mechanism guard is rotatable between: a first position wherein the cutter mechanism guard surrounds at least a portion of the cutting edge and prevents the cutting edge from engaging the occlusive material; and a second position wherein the cutter mechanism exposes the portion of the cutting edge to enable the cutting edge to engage and remove the occlusive material, wherein rotation of the drive shaft generates friction and vortex flow within the fluid in the fluid-filled tubular structure, and wherein the friction and the vortex flow cause the cutter mechanism guard to rotate between the first position and the second position.

12. The rotational device of embodiment 6, further comprising a helix-wound wire extending around at least a portion of an outer diameter of the drive shaft, wherein the helix-wound wire forces fluid and removed occlusive material proximally through an inner lumen defined by the sheath when the cutter mechanism is rotated within the fluid-filled tubular structure such that the cutting edge engages the occlusive material.

13. The rotational device of embodiment 6, further comprising a pull wire, the pull wire defining a proximal portion extending proximally of the sheath and a distal portion extending longitudinally within a wall of the sheath to the distal section of the sheath.

14. The rotational device of embodiment 13, wherein a proximal pulling force applied to the proximal portion of the pull wire causes the distal section of the sheath to deflect.

15. The rotational device of embodiment 14, wherein the deflection of the distal section of the sheath moves the distal section of the sheath into contact with an inner surface of the fluid-filled tubular structure opposite the lesion such that the cutting edge is forced into the occlusive material.

16. The rotational device of embodiment 1, further comprising a flexible distal tip coupled to the distal section of the drive shaft.

17. A system comprising the rotational device of embodiment 6, the system further comprising a roller pump coupled to the device and configured to create a plurality of vacuum pressures to draw fluid and removed occlusive material proximally through a lumen defined by the sheath.

18. The system of embodiment 17, further comprising a collection bag coupled to the device via a fluid line, the collection bag configured to receive the fluid and removed occlusive material drawn proximally through the lumen of the sheath, the collection bag comprising a plurality of graduated volumetric markings.

19. The system of embodiment 18, further comprising means for obtaining current and torque feedback from the device to enable determination of location and cutting capability.

20. The system of embodiment 17, further comprising a handle coupled to the device, the handle comprising a prime mover configured to drive rotation of the drive shaft.

21. The system of embodiment 20, wherein the handle further comprises a trigger coupled to the pull wire to control deflection of the distal section of the sheath.

22. The system of embodiment 20, further comprising a guide wire, wherein the handle further comprises a guide wire management system comprising one of an external guide wire brake and a pre-loaded torquer.

Embodiments Comprising a Multi-Stage Macerator

1. A rotational device for removing occlusive material within a fluid-filled tubular structure, comprising: a drive shaft configured for insertion into the fluid-filled tubular structure, the drive shaft defining a distal section; a cutter mechanism coupled to the distal section of the drive shaft such that the cutter mechanism rotates when the drive shaft rotates, the cutter mechanism comprising a cutting edge configured to remove occlusive material from a lesion within the fluid-filled tubular structure when the drive shaft is rotated and the cutter mechanism is positioned in engagement with the occlusive material; and a multi-stage macerator configured to macerate occlusive material removed from the lesion, the multi-stage macerator comprising: a first stage coupled to the drive shaft proximal to the cutting edge, the first stage configured to macerate occlusive material removed from the lesion and proximally force the macerated material when the drive shaft is rotated; a second stage coupled to the drive shaft proximal to the first stage, the second stage configured to receive the macerated occlusive material from the first stage, cut the macerated occlusive material into smaller pieces of occlusive material, and proximally force the smaller pieces when the drive shaft is rotated; and a third stage coupled to the drive shaft proximal to the second stage, the third stage configured to receive the smaller pieces of occlusive material from the second stage and cut the smaller pieces of occlusive material into smaller particles of occlusive material when the drive shaft is rotated.

2. The rotational device of embodiment 1, wherein the cutter mechanism further comprises a cutting ring base proximal to the cutting edge, wherein the first stage comprises a plurality of curved cutting hooks positioned within an inner diameter of the cutting ring base, and wherein the plurality of curved cutting hooks rotate when the cutter mechanism rotates.

3. The rotational device of embodiment 2, further comprising a cutter mechanism guard coupled to the distal section of the drive shaft radially outwardly from the cutter mechanism, the cutter mechanism guard defining a sharp edge, and wherein the sharp edge of the cutter mechanism guard is configured to assist the plurality of curved cutting hooks in macerating the occlusive material removed from the lesion by the cutting edge.

4. The rotational device of embodiment 2, wherein the second stage comprises a macerator body comprising a plurality of rotatable cutting edges, and wherein the plurality of rotatable cutting edges interact with the plurality of curved cutting hooks of the cutting ring base to cut the macerated occlusive material into the smaller pieces of occlusive material.

5. The rotational device of embodiment 4, wherein the third stage comprises an impeller comprising at least one rotating cutting edge, and wherein the at least one rotating cutting edge of the impeller interacts with a plurality of stationary cutting edges at a proximal end of the macerator body to cut the smaller pieces of occlusive material from the second stage into the smaller particles of occlusive material.

6. The rotational device of embodiment 1, further comprising an elongate flexible sheath disposed radially outwardly of the drive shaft and defining a distal section positioned proximal to the cutter mechanism.

7. The rotational device of embodiment 6, wherein the multi-stage macerator generates a proximal flow of fluid and the smaller particles of occlusive material from the impeller to an inner lumen defined by the sheath when the cutter mechanism is rotated within the fluid-filled tubular structure.

8. The rotational device of embodiment 7, wherein the cutter mechanism defines a cup shape and the cutter mechanism generates the proximal flow of fluid and removed occlusive material by generating a pressure differential between the fluid within the fluid-filled tubular structure and the lumen of the sheath.

9. The rotational device of embodiment 6, further comprising a helix-wound wire extending around at least a portion of an outer diameter of the drive shaft, wherein the helix-wound wire forces fluid and removed occlusive material proximally through an inner lumen defined by the sheath when the cutter mechanism is rotated within the fluid-filled tubular structure such that the cutting edge engages the occlusive material.

10. The rotational device of embodiment 6, further comprising a pull wire, the pull wire defining a proximal portion extending proximally of the sheath and a distal portion extending longitudinally within a wall of the sheath to the distal section of the sheath.

11. The rotational device of embodiment 10, wherein a proximal pulling force applied to the proximal portion of the pull wire causes the distal section of the sheath to deflect.

12. The rotational device of embodiment 11, wherein the deflection of the distal section of the sheath moves the distal section of the sheath into contact with an inner surface of the fluid-filled tubular structure opposite the lesion such that the cutting edge is forced into the occlusive material.

13. The rotational device of embodiment 1, further comprising a polyether ether ketone (PEEK) bushing near a junction of a distal end of the third stage of the macerator and the second stage of the macerator.

14. The rotational device of embodiment 1, further comprising a flexible distal tip coupled to the distal section of the drive shaft.

15. A system comprising the rotational device of embodiment 6, the system further comprising a roller pump coupled to the device and configured to create a plurality of vacuum pressures to draw fluid and removed occlusive material proximally through a lumen defined by the sheath.

16. The system of embodiment 15, further comprising a collection bag coupled to the device via a fluid line, the collection bag configured to receive the fluid and removed occlusive material drawn proximally through the lumen of the sheath, the collection bag comprising a plurality of graduated volumetric markings.

17. The system of embodiment 16, further comprising means for obtaining current and torque feedback from the device to enable determination of location and cutting capability.

18. The system of embodiment 15, further comprising a handle coupled to the device, the handle comprising a prime mover configured to drive rotation of the drive shaft.

19. The system of embodiment 18, wherein the handle further comprises a trigger coupled to the pull wire to control deflection of the distal section of the sheath.

20. The system of embodiment 20, further comprising a guide wire, wherein the handle further comprises a guide wire management system comprising one of an external guide wire brake and a pre-loaded torquer.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

We claim:

1. A rotational device for removing occlusive material within a fluid-filled tubular structure, comprising:
    a drive shaft configured for insertion into the fluid-filled tubular structure, the drive shaft defining a distal section;
    a cutter mechanism disposed on the distal section of the drive shaft such that the cutter mechanism rotates when the drive shaft rotates, the cutter mechanism comprising a cutting edge configured to remove occlusive material from within the fluid-filled tubular structure when the drive shaft is rotated and the cutter mechanism is positioned in engagement with the occlusive material;
    a cutter mechanism guard disposed on the distal section of the drive shaft, the cutter mechanism guard extending radially outwardly from the cutter mechanism and rotatable between:
        a first position wherein the cutter mechanism guard surrounds at least a portion of the cutting edge and prevents the cutting edge from engaging the occlusive material; and
        a second position wherein the cutter mechanism exposes the portion of the cutting edge to enable the cutting edge to engage and remove the occlusive material,
    wherein rotation of the drive shaft generates friction and vortex flow within the fluid in the fluid-filled tubular structure, and wherein the friction and the vortex flow cause the cutter mechanism guard to rotate between the first position and the second position;
    a distal tip coupled to the distal section of the drive shaft, the distal tip comprising an abrasive outer surface configured to abrade occlusive material from the fluid-filled tubular structure when the drive shaft is rotated; and
    a distal pull wire configured to enable steering of the distal tip, wherein the distal tip is steerable through at least two directions in a single plane of movement and through at least two planes of movement.

2. The rotational device of claim 1, further comprising an elongate flexible sheath disposed radially outwardly of the drive shaft and defining a distal section positioned proximal to the cutter mechanism.

3. The rotational device of claim 2, wherein the cutter mechanism generates a proximal flow of fluid and removed occlusive material from the cutter mechanism to a lumen defined by the sheath when the cutter mechanism is rotated within the fluid-filled tubular structure.

4. The rotational device of claim 2, further comprising a helix-wound wire extending around at least a portion of an outer diameter of the drive shaft, wherein the helix-wound wire forces fluid and removed occlusive material proximally through a lumen defined by the sheath when the cutter mechanism is rotated within the fluid-filled tubular structure.

5. The rotational device of claim 2, further comprising a pull wire, the pull wire defining a proximal portion extending proximally of the sheath and a distal portion extending longitudinally within the sheath to the distal section of the sheath.

6. The rotational device of claim 5, wherein a proximal pulling force applied to the proximal portion of the pull wire causes the distal section of the sheath to deform to one of a Z-shape and an S-shape.

7. The rotational device of claim 1, wherein the distal tip is tapered such that a first outer diameter at a proximal end of the distal tip is greater than a second outer diameter at a distal end of the distal tip.

8. The rotational device of claim 1, wherein an outer surface defined by the distal tip comprises a diamond coating.

9. The rotational device of claim 1, wherein the distal tip is approximately 2-4 millimeters distal of the cutting edge.

10. The rotational device of claim 1, wherein the distal tip is steerable to maintain the cutter mechanism substantially parallel to an inner diameter of the fluid-filled tubular structure.

11. A system comprising the rotational device of claim 1, the system further comprising a roller pump coupled to the device and configured to create a plurality of vacuum pressures to draw fluid and removed occlusive material proximally through a lumen defined by the sheath.

12. The system of claim 11, further comprising a collection bag coupled to the device and configured to receive the fluid and removed occlusive material drawn proximally through the lumen of the sheath, the collection bag comprising a plurality of graduated volumetric markings.

13. The system of claim 1, further comprising a handle coupled to the device, the handle comprising a prime mover configured to drive rotation of the drive shaft.

14. A rotational device for removing occlusive material within a fluid-filled tubular structure, comprising:
- a drive shaft configured for insertion into the fluid-filled tubular structure, the drive shaft defining a distal section;
- a cutter mechanism disposed on the distal section of the drive shaft such that the cutter mechanism rotates when the drive shaft rotates, the cutter mechanism comprising a cutting edge configured to remove occlusive material from a lesion within the fluid-filled tubular structure when the drive shaft is rotated and the cutter mechanism is positioned in engagement with the occlusive material; and
- a distal nosecone coupled to the distal section of the drive shaft extending distally of the cutting edge, wherein the distal nosecone defines a tapered profile such that a first outer diameter at a proximal end of the distal nosecone is greater than a second outer diameter at a distal end of the distal nosecone,
- wherein the distal nosecone is configured to limit the depth to which the cutting edge penetrates the lesion during removal of the occlusive material from the lesion, and wherein the tapered profile of the distal nosecone is configured to draw occlusive material proximally toward the cutting edge as the distal nosecone is advanced along the lesion, and
- wherein the distal nosecone defines an abrasive outer surface configured to abrade occlusive material from the fluid-filled tubular structure when the drive shaft is rotated,
- wherein the distal nosecone is configured to limit the depth to which the cutting edge penetrates the lesion to a difference between the first diameter of the distal nosecone and a diameter of the cutter mechanism at the cutting edge.

15. The rotational device of claim 14, wherein the distal nosecone is approximately 2-4 millimeters distal of the cutting edge.

16. The rotational device of claim 14, further comprising a distal pull wire configured to enable steering of the distal nosecone, wherein the distal nosecone is steerable through at least two directions in a single plane of movement and through at least two planes of movement.

17. The rotational device of claim 16, wherein the distal nosecone is configured to be steerable to maintain the cutter mechanism substantially parallel to an inner diameter of the fluid-filled tubular structure.

18. The rotational device of claim 14, further comprising an elongate flexible sheath defining a lumen and a distal section positioned proximal to the cutter mechanism, the drive shaft at least partially received within the lumen.

19. The rotational device of claim 18, wherein the cutter mechanism generates a proximal flow of fluid and removed occlusive material from the cutter mechanism to a lumen defined by the sheath when the cutter mechanism is rotated within the fluid-filled tubular structure.

20. The rotational device of claim 18, further comprising a helix-wound wire extending around at least a portion of an outer diameter of the drive shaft, wherein the helix-wound wire is configured to force fluid and removed occlusive material proximally through a lumen defined by the sheath when the cutter mechanism is rotated within the fluid-filled tubular structure.

21. The rotational device of claim 18, further comprising a pull wire, the pull wire defining a proximal portion extending proximally of the sheath and a distal portion extending longitudinally within the sheath to the distal section of the sheath.

22. The rotational device of claim 21, wherein a proximal pulling force applied to the proximal portion of the pull wire causes the distal section of the sheath to deform to one of a Z-shape and an S-shape.

23. A rotational device for removing occlusive material within a fluid-filled tubular structure, comprising:
- a drive shaft configured for insertion into the fluid-filled tubular structure, the drive shaft defining a distal section;
- a cutter mechanism coupled to the distal section of the drive shaft such that the cutter mechanism rotates when the drive shaft rotates, the cutter mechanism comprising:
  - a sharp distal cutting edge configured to cut non-calcified occlusive material from within the fluid-filled tubular structure when the drive shaft is rotated and the sharp distal cutting edge is positioned in engagement with the non-calcified occlusive material;
  - a major outer surface coated with an abrasive composition and configured to abrade calcified occlusive material from within the fluid-filled tubular structure when the drive shaft is rotated and the abrasive surface of the cutter mechanism is positioned in engagement with the calcified occlusive material,
- wherein the cutter mechanism generates a proximal flow of fluid and removed occlusive material from the cutter mechanism to an inner lumen defined by the sheath when the cutter mechanism is rotated within the fluid-filled tubular structure; and an elongate flexible sheath disposed radially outwardly of the drive shaft and defining a distal section positioned proximal to the cutter mechanism, and wherein the cutter mechanism defines a cup shape and the cutter mechanism generates the proximal flow of fluid and removed occlusive material by generating a pressure differential between the fluid within the fluid-filled tubular structure and the lumen of the sheath.

24. The rotational device of claim 23, wherein the cutter mechanism comprises at least two materials having different compositions and different hardnesses.

25. A rotational device for removing occlusive material within a fluid-filled tubular structure, comprising:
   a drive shaft configured for insertion into the fluid-filled tubular structure, the drive shaft defining a distal section;
   a cutter mechanism coupled to the distal section of the drive shaft such that the cutter mechanism rotates when the drive shaft rotates, the cutter mechanism comprising a cutting edge configured to remove occlusive material from a lesion within the fluid-filled tubular structure when the drive shaft is rotated and the cutter mechanism is positioned in engagement with the occlusive material; and
   a multi-stage macerator configured to macerate occlusive material removed from the lesion, the multi-stage macerator comprising:
      a first stage coupled to the drive shaft proximal to the cutting edge, the first stage configured to macerate occlusive material removed from the lesion and proximally force the macerated material when the drive shaft is rotated;
      a second stage coupled to the drive shaft proximal to the first stage, the second stage configured to receive the macerated occlusive material from the first stage, cut the macerated occlusive material into smaller pieces of occlusive material, and proximally force the smaller pieces when the drive shaft is rotated; and
      a third stage coupled to the drive shaft proximal to the second stage, the third stage configured to receive the smaller pieces of occlusive material from the second stage and cut the smaller pieces of occlusive material into smaller particles of occlusive material when the drive shaft is rotated;
   a distal pull wire configured to enable steering of the distal tip, wherein the distal tip is steerable through at least two directions in a single plane of movement and through at least two planes of movement, wherein the distal tip is steerable to maintain the cutter mechanism substantially parallel to an inner surface of the fluid-filled tubular structure.

26. The rotational device of claim 25, wherein the first stage comprises a plurality of curved cutting hooks positioned within an inner diameter of the cutter mechanism.

27. The rotational device of claim 25, wherein the second stage comprises a macerator body comprising a plurality of stationary cutting edges and a plurality of rotating cutting edges.

28. The rotational device of claim 25, wherein the third stage comprises an impeller comprising at least one rotating cutting edge.

29. The rotational device of claim 25, further comprising an elongate flexible sheath disposed radially outwardly of the drive shaft and defining a distal section positioned proximal to the cutter mechanism.

30. The rotational device of claim 25, wherein the multi-stage macerator generates a proximal flow of fluid and the smaller particles of occlusive material from the impeller to an inner lumen defined by the sheath when the cutter mechanism is rotated within the fluid-filled tubular structure.

31. The rotational device of claim 25, wherein the cutter mechanism defines a cup shape and the cutter mechanism generates the proximal flow of fluid and removed occlusive material by generating a pressure differential between the fluid within the fluid-filled tubular structure and the lumen of the sheath.

32. The rotational device of claim 25, further comprising a helix-wound wire extending around at least a portion of an outer diameter of the drive shaft, wherein the helix-wound wire forces fluid and removed occlusive material proximally through an inner lumen defined by the sheath when the cutter mechanism is rotated within the fluid-filled tubular structure such that the cutting edge engages the occlusive material.

33. The rotational device of claim 25, further comprising a pull wire, the pull wire defining a proximal portion extending proximally of the sheath and a distal portion extending longitudinally within the sheath to the distal section of the sheath.

34. The rotational device of claim 33, wherein a proximal pulling force applied to the proximal portion of the pull wire causes the distal section of the sheath to deform to one of a Z-shape and an S-shape.

35. The rotational device of claim 25, further comprising a distal tip coupled to the distal section of the drive shaft, the distal tip comprising an abrasive outer surface configured to abrade occlusive material from the fluid-filled tubular structure when the drive shaft is rotated.

36. A system comprising the rotational device of claim 25, the system further comprising a roller pump coupled to the device and configured to create a plurality of vacuum pressures to draw fluid and removed occlusive material proximally through an inner lumen defined by the sheath.

37. The system of claim 25, further comprising a handle coupled to the device, the handle comprising a prime mover configured to drive rotation of the drive shaft.

* * * * *